(12) United States Patent
Coats et al.

(10) Patent No.: US 10,828,270 B2
(45) Date of Patent: *Nov. 10, 2020

(54) OXPRENOLOL COMPOSITIONS FOR TREATING CANCER

(71) Applicant: Actimed Therapeutics Limited, Ascot (GB)

(72) Inventors: Andrew J. S. Coats, St. Kilda (AU); Stefan Anker, Berlin (DE); Jochen Springer, Falkensee (DE)

(73) Assignee: Actimed Therapeutics Limited, Ascot (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/923,872

(22) Filed: Mar. 16, 2018

(65) Prior Publication Data

US 2019/0054043 A1 Feb. 21, 2019

Related U.S. Application Data

(63) Continuation of application No. 14/776,020, filed as application No. PCT/AU2014/000266 on Mar. 14, 2014, now Pat. No. 10,398,658.

(60) Provisional application No. 61/786,241, filed on Mar. 14, 2013.

(51) Int. Cl.
*A61K 31/138* (2006.01)

(52) U.S. Cl.
CPC .................. *A61K 31/138* (2013.01)

(58) Field of Classification Search
CPC ......... A61K 31/138; A61P 21/00; A61P 35/00
See application file for complete search history.

(56) References Cited

U.S. PATENT DOCUMENTS

| 7,417,038 B1 | 8/2008 | Anker et al. |
| 2005/0143378 A1 | 6/2005 | Yun et al. |
| 2012/0082659 A1 | 4/2012 | Land et al. |
| 2012/0095070 A1 | 4/2012 | Springer et al. |
| 2012/0178757 A1 | 7/2012 | Powe |

FOREIGN PATENT DOCUMENTS

| CN | 101323580 A | 12/2008 |
| EP | 0930291 B1 | 8/2002 |
| WO | 1996/033162 A1 | 10/1996 |
| WO | 2000/021509 A2 | 4/2000 |

OTHER PUBLICATIONS

International Search Report of PCT/AU2014/000266 dated May 13, 2014, 3 pages.
Martinez-Gomez et al., "Chiral separation of oxprenolol by affinity electrokinetic chromatography-partial filling technique using human serum albumin as chiral selector", J Pharmaceutical and Biomedical Analysis, Sep. 1, 2005, vol. 39, Nos. 1-2, pp. 76-81.
Dong et al., "Pharmacokinetics of Chiral Drugs", Chiral Drugs: Chemistry and Biological Action, First Edition, 2011, pp. 347-379.
Sausville et al., "Contributions of Human Tumor Xenografts to Anticancer Drug Development", Cancer Research, Apr. 1, 2006, vol. 66, No. 7, pp. 3351-3354.
Johnson et al., "Relationships between drug activity in NCI preclinical in vitro and in vivo models and early clinical trials", British Journal of Cancer, 2001, vol. 84, No. 10, pp. 1424-1431.

*Primary Examiner* — Umamaheswari Ramachandran
(74) *Attorney, Agent, or Firm* — MH2 Technology Law Group, LLP

(57) ABSTRACT

The present invention relates to compositions of S-enantiomer enriched oxprenolol and their use in treating cancer and treating or preventing, in cancer patients, cachexia, body weight loss, lean body mass loss and adipose tissue loss, and improving quality of life and prolonging survival of cancer patients.

16 Claims, 25 Drawing Sheets

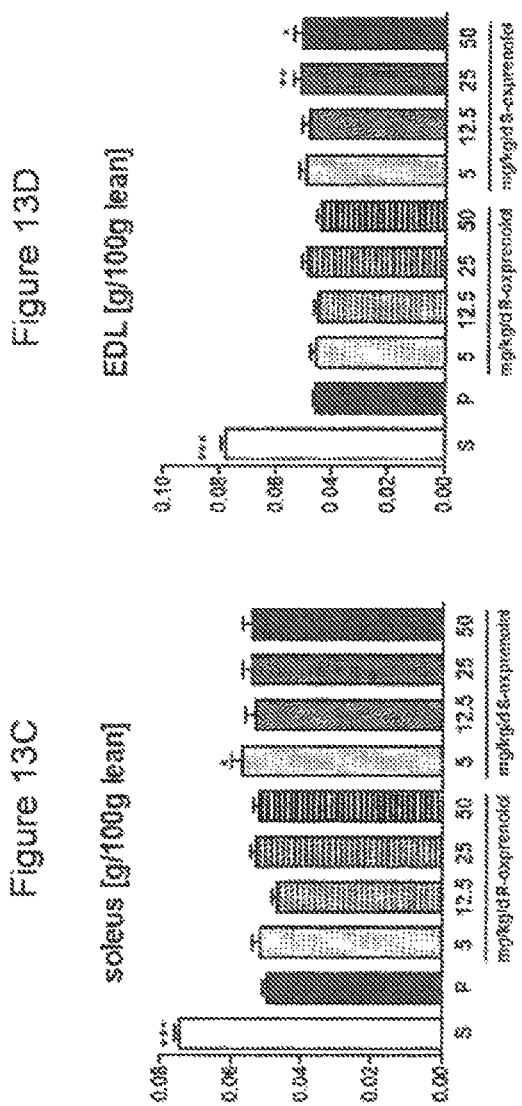

WAT [g]

BAT [g]

*: p<0.05, ***: p<0.001 vs placebo
: p<0.05 vs 20 mg S-oxprenolol

OXPRENOLOL COMPOSITIONS FOR TREATING CANCER

CROSS REFERENCE TO RELATED APPLICATIONS

This application is a continuation of U.S. application Ser. No. 14/776,020 (Allowed), filed 14 Sep. 2015, which is a U.S. National Stage Application of PCT/AU2014/000266, filed 14 Mar. 2014, which claims the priority benefit of U.S. Provisional Patent Application Ser. No. 61/786,2241, filed Mar. 14, 2013, which is incorporated herein by reference in its entirety.

TECHNICAL FIELD

The present invention relates to oxprenolol compositions and uses thereof, including uses of the oxprenolol compositions for treating cancer.

BACKGROUND

Cancer is the second most common cause of death in the United States, exceeded only by heart disease. In the United States, cancer accounts for 1 of every 4 deaths. With population growth and aging of the population, the number of new cancer patients is expected to double to 2.6 million people by 2050.

Liver cancer is the sixth most common cancer worldwide and the third most common cause of cancer-related death. The most common form of liver cancer is hepatocellular carcinoma (HCC). HCC is often diagnosed late in the course of clinical manifestation. As a result, only 10-15% of patients are candidates for curative surgery. For the majority of HCC patients, systemic chemotherapies or supportive therapies are the mainstay treatment options. Nevertheless, most, chemotherapeutic agents show limited effectiveness and have not been able to improve patient survival. See, e.g. Ma Y T. Palmer D H. Impact of restricting access to high-cost medications for hepatocellular carcinoma. [Review] Expert Review of Pharmacoeconomics & Outcomes Research. 12(4):465-73, 2012 August.

Oxprenolol is a non-selective beta blocker which possesses some intrinsic sympathomimetic activity. Because of its beta blocker function, oxprenolol has been used for the treatment of various diseases such as angina pectoris, abnormal heart rhythms, and high blood pressure. Oxprenolol is lipophilic and crosses the blood-brain barrier more easily than other more water soluble beta blockers. As a result, oxprenolol is associated with a higher incidence of CNS-related side effects than other beta blockers, but also has more central CNS modes of action.

The disclosure of all publications, patents, patent applications, and published patent applications referred to herein are hereby incorporated herein by reference in their entirety.

BRIEF SUMMARY OF THE INVENTION

The present invention relates to oxprenolol compositions and uses thereof, including uses of the oxprenolol compositions for treating cancer.

The present disclosure provides, in some embodiments, a method of treating cancer in an individual having cancer, comprising administering to the individual an effective amount of a composition comprising oxprenolol or a pharmaceutically acceptable salt thereof, wherein the composition is enantiomerically enriched for S-oxprenolol.

The present disclosure provides, in some embodiments, a method of prolonging survival of an individual having cancer, comprising administering to the individual an effective amount of a composition comprising oxprenolol or a pharmaceutically acceptable salt thereof, wherein the composition is enantiomerically enriched for S-oxprenolol.

The present disclosure provides, in some embodiments, a method of preventing body weight loss of an individual having cancer, comprising administering to the individual an effective amount of a composition comprising oxprenolol or a pharmaceutically acceptable salt thereof, wherein the composition is enantiomerically enriched for S-oxprenolol.

The present disclosure provides, in some embodiments, a method of improving quality of life in an individual having cancer, comprising administering to the individual an effective amount of a composition comprising oxprenolol or a pharmaceutically acceptable salt thereof, wherein the composition is enantiomerically enriched for S-oxprenolol.

The present disclosure provides, in some embodiments, a method of preventing and/or treating loss of lean body mass in an individual having cancer, comprising administering to the individual an effective amount of a composition comprising oxprenolol or a pharmaceutically acceptable salt thereof, wherein the composition is enantiomerically enriched for S-oxprenolol.

The present disclosure provides, in some embodiments, a method of preventing and/or treating muscle wasting in an individual having cancer, comprising administering to the individual an effective amount of a composition comprising oxprenolol or a pharmaceutically acceptable salt thereof, wherein the composition is enantiomerically enriched for S-oxprenolol.

In some embodiments, the individual has no symptom of cancer cachexia. In some embodiments, the individual has one or more symptoms of cancer cachexia. In some embodiments, the composition comprises an enantiomeric excess of at least about 50% of S-oxprenolol. In some embodiments, the composition comprises an enantiomeric excess of at least about 80% of S-oxprenolol. In some embodiments, the composition comprises an enantiomeric excess of at least about 99% of S-oxprenolol. In some embodiments, the composition comprises an enantiomeric excess of at least 99.9% of S-oxprenolol. In some embodiments, the cancer is selected from the group consisting of liver cancer, lung cancer, ovarian cancer, pancreatic cancer, melanoma, and brain cancer. In some embodiments, the cancer is selected from the group consisting of gastric cancer, pancreatic cancer, lung, esophageal, colorectal, head and neck cancer, and hematological malignancies. In some embodiments, the cancer is liver cancer. In some embodiments, the cancer is an early stage cancer. In some embodiments, the cancer is a late stage cancer. In some embodiments, the composition is administered orally. In some embodiments, the amount of S-oxprenolol in the composition is about 80 to about 160 mg daily. In some embodiments, the composition is administered daily or twice daily.

The present disclosure provides, in some embodiments, a pharmaceutical composition comprising oxprenolol or a pharmaceutically acceptable salt thereof and a pharmaceutically acceptable carrier, wherein the composition is enantiomerically enriched for S-oxprenolol.

In some embodiments, the composition comprises an enantiomeric excess of at least about 50% of S-oxprenolol. In some embodiments, the composition comprises an enantiomeric excess of at least about 80% of S-oxprenolol. In some embodiments, the composition comprises an enantiomeric excess of at least about 99% of S-oxprenolol.

In some embodiments, the composition comprises an enantiomeric excess of at least 99.9% of S-oxprenolol.

The present disclosure provides, in some embodiments, a kit comprising a pharmaceutical composition comprising oxprenolol or a pharmaceutically acceptable salt thereof and a pharmaceutically acceptable carrier, wherein the composition is enantiomerically enriched for S-oxprenolol and instruction for using the pharmaceutical composition for treating cancer.

BRIEF DESCRIPTION OF THE FIGURES

FIG. 13C is a graph showing the mass of soleus muscle (in grams per 100 grams of lean muscle mass ("g/100 g lean")) in rat populations that were administered with various dosages of S-oxprenolol or R-oxprenolol at the endpoint of the study. FIG. 13D is a graph showing the mass of extensor digitorum longus (EDL) muscle (in grams per 100 grams of lean muscle mass ("g/100 g lean")) in rat populations that were administered with various dosages of S-oxprenolol or R-oxprenolol at the endpoint of the study. Comparison to placebo (P) and sham (S) was also provided. The asterisk (*) indicates p<0.05 versus placebo. The two asterisks () indicate p<0.01 versus placebo. The three asterisks (*) indicate p<0.001 versus placebo.

DETAILED DESCRIPTION OF THE INVENTION

Figure 1:
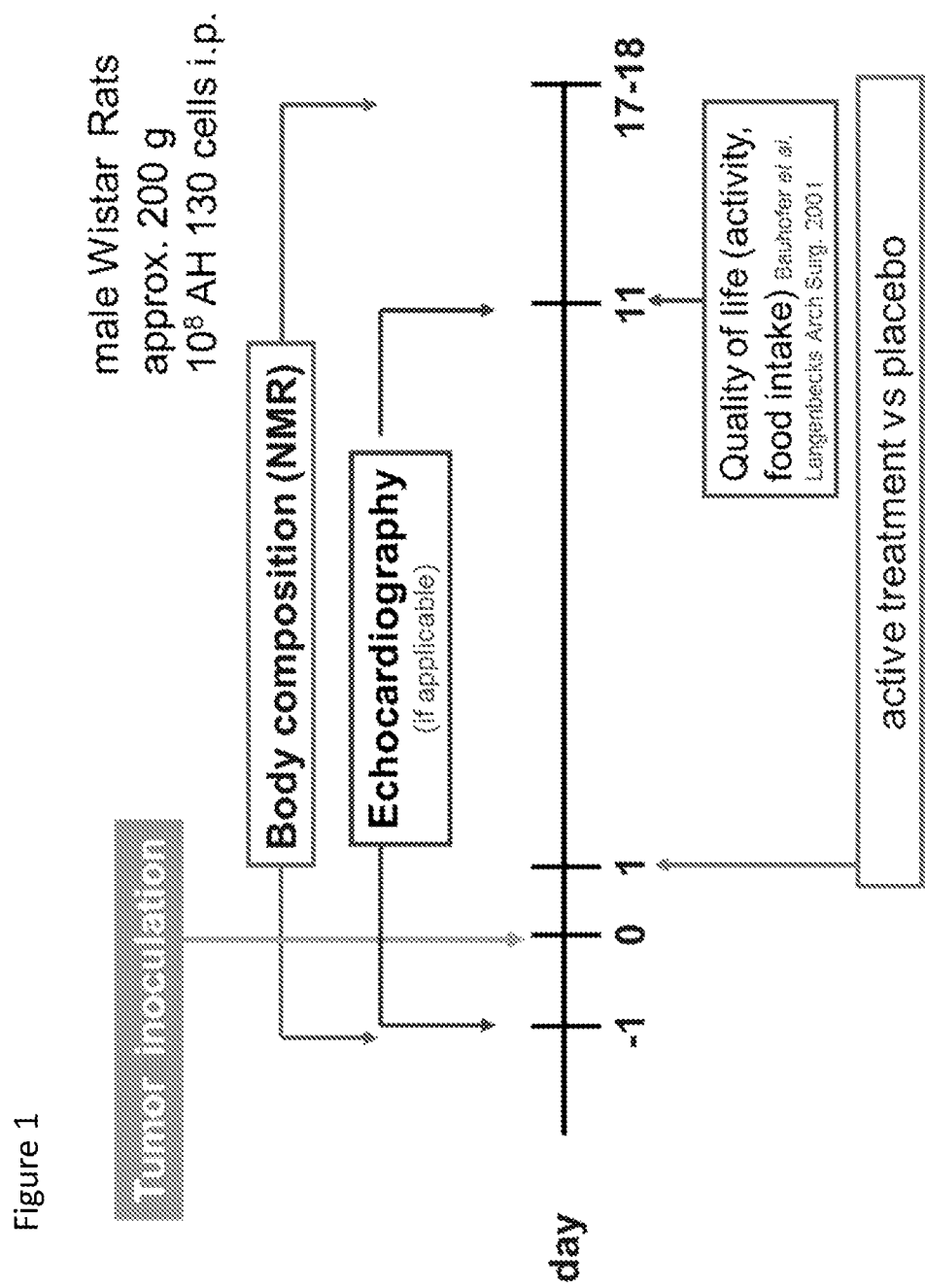
FIG. 1 is a diagram of the design study involving the Yoshida Hepatoma Model for cancer cachexia.

The present invention provides use of enantiomerically enriched S-oxprenolol compositions for achieving beneficial results in individuals having cancer, such as treating cancer, prolonging survival, preventing body weight loss, improving quality of life, and/or treating muscle wasting. Also provided are pharmaceutical compositions of oxprenolol that are enantiomerically enriched S-oxprenolol.

The present invention is based on the surprising finding that S-oxprenolol, but not R-oxprenolol, significantly improved survival in animals having cancer in an experiment in which an animal was inoculated with hepatocellular carcinoma cells in a well-established animal model of hepatoma. We have further surprisingly found that S-oxprenolol, when provided in isolated forms in the same amount as those present in a racemic mixture, had an improved effect on survival than the racemic mixture. Similar differential effects of the compositions were observed on preventing body weight loss, preserving lean body mass, and preserving fat mass in the animals. These differential effects suggest that S-oxprenolol is significantly more effective in treating cancer and prolonging survival when present in an enantiomerically enriched composition. Moreover, these differential effects were observed in animals not developing cachexia or before the animals develop cachexia, suggesting that at least some of the effect of S-oxprenolol we observed may be independent and/or in addition to its effect on treating cancer cachexia.

Thus, the present invention in one aspect provides methods of treating cancer, prolonging survival, preventing body weight loss, preventing and/or treating muscle wasting, or improving quality of life in an individual having cancer, comprising administering to the individual an effective amount of a composition comprising oxprenolol or a pharmaceutically acceptable salt thereof, wherein the composition is enantiomerically enriched for S-oxprenolol.

In another aspect, there are provided pharmaceutical compositions comprising oxprenolol or a pharmaceutically acceptable salt thereof and a pharmaceutically acceptable carrier, wherein the composition is enantiomerically enriched for S-oxprenolol.

Also provided are kits, unit dosages, medicines, and articles of manufacture that are useful for methods described herein.

Definitions

The following terms have the following meanings unless otherwise indicated. Any undefined terms have their art recognized meanings.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, delay or slowing the progression of the disease, ameliorating the disease state, delaying the progression of the disease, increasing the quality of life, and/or prolonging survival. Also encompassed by "treatment" is a reduction of pathological consequence of cancer. The methods of the invention contemplate any one or more of these aspects of treatment.

The term "individual" refers to a mammal and includes, but is not limited to, human, bovine, horse, feline, canine, rodent, or primate. In some embodiments, the individual is a human.

As used herein, an "at risk" individual is an individual who is at risk of developing cancer. An individual "at risk" may or may not have detectable disease, and may or may not have displayed detectable disease prior to the treatment methods described herein. "At risk" denotes that an individual has one or more so-called risk factors, which are measurable parameters that correlate with development of cancer. An individual having one or more of these risk factors has a higher probability of developing cancer than an individual without these risk factor(s).

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is earned out before the primary/definitive therapy.

As used herein, "delaying" the development of a disease means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of a disease is a method that reduces probability of disease development in a given time frame and/or reduces the extent of the disease in a given time frame, when compared to not using the method. Such comparisons are typically based on clinical studies, using a statistically significant number of subjects.

As used herein, by "combination therapy" is meant that a first agent be administered in conjunction with another agent. "In conjunction with" refers to administration of one treatment modality in addition to another treatment modality, such as administration of a nanoparticle composition described herein in addition to administration of the other agent to the same individual. As such, "in conjunction with" refers to administration of one treatment modality before, during, or after delivery of the other treatment modality to the individual. Such combinations are considered to be part of a single treatment regimen or regime.

The term "effective amount" used herein refers to an amount of a compound or composition sufficient to treat a specified disorder, condition or disease such as ameliorate, palliate, lessen, and/or delay one or more of its symptoms.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to an individual without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Progression free survival" (PFS) indicates the length of rime during and after treatment that the cancer does not grow. Progression-free survival includes the amount of time individuals have experienced a complete response or a partial response, as well as the amount of time individuals have experienced stable disease, in some embodiments, an individual has a capacity to accept more courses of chemotherapy during progression free survival.

The term "isomers" or "stereoisomers" refers to compounds which have identical chemical constitution, but differ with regard to the arrangement of the atoms or groups in space.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "enantiomerically enriched" means that to the racemic mixture (i.e., 50/50 mixture of the enantiomers) has been purified such that one enantiomer comprises greater than 50% of the total amount of the compound present. For example, a composition that is enantiomerically enriched for S-oxprenolol is a composition wherein more than 50% of the oxprenolol is the S-enantiomer of oxprenolol (S-oxprenolol).

The degree of enantiomeric enrichment of a composition can be determined by "enantiomeric excess," or ee, "Enantiomeric excess" represents the percentage of one enantiomer in excess of the other. For instance, a composition having a 75:25 mixture of S-oxprenolol and R-oxprenolol has a 75-25=50% ee, while a 50:50 racemic mixture has a 50–50=0% ee. The value of ee will be a number from 0 to 100, 0 being racemic and 100 being pure, single enantiomer.

The term "pharmaceutically acceptable salt" means a salt which is acceptable for administration to a subject, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to the subject. By way of example, salts of the present compounds include those wherein the compound is protonated by an inorganic or organic acid to form a cation, with the conjugate base of the inorganic or organic acid as the anionic component of the stilt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

It will be appreciated that the term "or a salt or solvate thereof" is intended to include all permutations of salts and solvates, such as a solvate of a pharmaceutically acceptable salt of a subject compound.

As used herein, "in conjunction with" refers to administration of one treatment modality in addition to another treatment modality. As such, "in conjunction with" refers to administration of one treatment modality before, during or after administration of the other treatment modality to the individual.

As used herein and in the appended claims, the singular forms "a," "an," and "the" include plural reference unless the context clearly indicates otherwise.

Reference to "about" a value or parameter herein includes (and describes) embodiments that are directed to that value or parameter per se. For example, description referring to "about X" includes description of "X."

It is understood that aspects and variations of the invention described herein include "consisting" and/or "consisting essentially of" aspects and variations.

Methods of the Present Invention

The present application in one aspect provides methods of treating cancer. In some embodiments, there is provided a method of treating cancer in an individual having cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of treating cancer in an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of treating cancer in an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, there is provided a method of prolonging survival of an individual having cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of prolonging survival in an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of prolonging survival of an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia, in some embodiments, the individual has one or more symptoms of cancer cachexia. In some embodiments, the method prolongs the survival of the individual by at least any of 1, 2, 3, 4, 5, 6, 7, 8, 9, 10, 11, 12, 18, or 24 months.

In some embodiments, there is provided a method of prolonging progression-free survival in an individual with cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided method of prolonging progression-free survival in an individual with cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided method of prolonging progression-free survival in an individual with cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, there is provided a method of alleviating one or more symptoms associated with cancer in an individual, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided method of alleviating one or more symptoms associated with cancer in an individual, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided method of alleviating one or more symptoms associated with cancer in an individual, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, there is provided a method of preventing body weight loss of an individual having cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of preventing body weight loss in an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of preventing body weight loss of an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia. In some embodiments, the body weight loss of the individual is no more than about 20% (for example no more than about any of 15%, 14%, 13%, 12%, 11%, 10%, 9%, 8%, 7%, 6%, or 5%) of the total body weight. In some embodiments, the body weight loss is evaluated over a time period of about 1 month to 2 years (for example, about 1, 2, 3, 4, 5, 6, 7, 8, 9, 10, 11, 12, 1.3, 14, 15, 16, 17, 18, 19, 20, 21, 22, 23, or 24 months).

In some embodiments, there is provided a method of treating muscle wasting in an individual having cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of treating muscle wasting in an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of treating muscle wasting in an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia, in some embodiments, the muscle wasting of the individual is no more than about 1.0% (for example no more than about any of 10%, 9%, 8%, 7%, 6%, or 5%) of the total body weight. In some embodiments, the muscle wasting is evaluated over a time period of about 1 month to 2 years (for example, about 1, 2, 3, 4, 5, 6, 7, 8, 9, 10, 11, 12, 13, 14, 1.5, 16, 17, 18, 19, 20, 21, 22, 23, or 24 months). In some embodiments, the method leads to a reduction of muscle wasting, i.e., a slow-down of muscle loss in the individual. In some embodiments, the method leads to a reversal of muscle wasting, i.e., an increase in muscle weight in the individual.

In some embodiments, there is provided a method of preventing loss of lean body mass in an individual having cancer, comprising administering to the individual an effective amount of a composition comprising oxprenolol or a pharmaceutically acceptable salt thereof, wherein the composition is enantiomerically enriched for S-oxprenolol. In some embodiments, there is provided a method of treating loss of lean body mass in an individual having cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of preventing loss of lean body mass in an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of preventing loss of lean body mass in an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia. In some embodiments, the loss of lean body mass of the individual is no more than about 10% (for example no more than about any of 10%, 9%, 8%, 7%, 6%, or 5%) of the total lean body mass. In some embodiments, the loss of lean body mass is evaluated over a time period of about 1 month to 2 years (for example, about 1, 2, 3, 4, 5, 6, 7, 8, 9, 10, 11, 12, 13, 14, 15, 16, 17, 18, 19, 20, 21, 22, 23, or 24 months).

In some embodiments, there is provided a method of preventing (or delaying) development of cancer cachexia in an individual having cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of preventing (or delaying) the development of cachexia in an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of preventing (or delaying) development of cancer cachexia in an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, the individual has one or more symptoms of cancer cachexia, and the methods described herein can be used to improve one or more symptoms of cancer cachexia in an individual having cancer, the methods comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of improving one or more symptoms of cancer cachexia in an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of a method of improving one or more symptoms of cancer cachexia in an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia. Symptoms of cachexia include but not limited to, loss of weight, muscle atrophy, fatigue, weakness, and loss of appetite.

In some embodiments, there is provided a method of improving quality of life of an individual having cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of improving quality of life of an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of improving quality of life of an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia. Improvement of quality of life can be assessed, for example, by food intake, locomotive activity, improvement in fatigue or dyspnea or global patient assessment scores, in short physical performance battery scores, in standard clinical assessment of functional performance, muscle strength, gait speed, leg strength and hand grip strength, 6-minute corridor walk test, stair climbing power, ability to tolerate courses of chemotherapy and other tests or instruments or questionnaires assessing patient quality of life.

In some embodiments, there is provided a method of increasing food intake of an individual having cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of increasing food intake of an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of increasing food intake of an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, there is provided a method of increasing locomotive activity of an individual having cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of increasing locomotive activity of an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of increasing locomotive activity of an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, there is provided a method of improving fatigue or dyspnea in an individual having cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of improving fatigue or dyspnea in an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of improving fatigue or dyspnea in an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, there is provided a method of preventing loss of body fat in an individual having cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of preventing loss of body fat in an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of preventing loss of body fat in an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia. In some embodiments, the loss of body fat of the individual is no more than about 10% (for example no more than about any of 15%, 14%, 13%, 12%, 11%, 10%, 9%, 8%, 7%, 6%, or 5%) of the total body fat. In some embodiments, the loss of body fat is evaluated over a time period of about 1 month to 2 years (for example, about 1, 2, 3, 4, 5, 6, 7, 8, 9, 10, 11, 12, 13, 14, 15, 16, 17, 18, 19, 20, 21, 22, 23, or 24 months).

Adipose tissue appears as two types: white adipose tissue and brown adipose tissue. White adipose tissue cells contain a single large fat droplet, which forces the nucleus to be squeezed into a thin rim at the periphery. They have receptors for insulin, growth hormones, norepinephrine and glucocorticoids. White adipose tissue is used as a store of energy. White adipose tissue also acts as a thermal insulator, helping to maintain body temperature. Brown adipose tissue cells contain numerous smaller droplets and a higher number of (iron containing) mitochondria, which gives a brown color to the cell. Brown fat also contains more capillaries than white fat, since it has a greater need for oxygen than most tissues. The methods provided herein are useful for preventing loss of both white adipose tissue and brown adipose tissue in an individual having cancer.

In some embodiments, there is provided a method of providing cardioprotective effects in an individual having cancer, comprising administering to the individual an effective amount of a composition comprising oxprenolol or a pharmaceutically acceptable salt thereof, wherein the composition is enantiomerically enriched for S-oxprenolol. In some embodiments, there is provided a method of pre venting wasting of a heart muscle in an individual having cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%=, 90%, 95%, 96%, 97%, 98%, or 99%) of S-oxprenolol. In some embodiments, there is provided a method of providing cardioprotective effects in an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of preventing wasting of a heart muscle in an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of providing cardioprotective effects in an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in tire composition is about 50 mg to about 160 mg (such as about 80 to about 160 mg, for example about 100 mg to about 160 mg). In some embodiments, there is provided a method of preventing wasting of a heart muscle in an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia. Cardioprotective effects include one or more of the following: preventing and treating atrial fibrillation and ventricular fibrillation, improving arrhythmias, improving diastolic function of a heart, and preventing and treating fibrosis of a heart. The methods described herein are therefore useful for any one or more of these cardioprotective effects.

In some embodiments, there is provided a method of preventing sudden death and/or cardiovascular death in an individual having cancer, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of preventing sudden death and/or cardiovascular death in an individual having cancer, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of preventing sudden death and/or cardiovascular death in an individual having cancer, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

The methods described herein may be useful for any one or more of the following: 1) preventing loss of skeletal muscle associated with cancer; 2) treating fatigue associated with cancer; 3) treating muscle weakness associated with cancer; 4) strengthening skeletal muscle in an individual having cancer; 5) treatment of muscle wasting associated with cancer; 6) treating dyspnea associated with muscle changes in cancer; and 7) improving fatigue resistance of muscle in cancer. Skeletal muscle includes, but is not limited to, gastrocnemius muscle, tibialis muscle, soleus muscle, and extensor digitorum longus (HDL) muscle, quadriceps, hamstrings, postural muscles, hand muscles, triceps, biceps, masseter and other jaw muscles, and intercostal and other respiratory muscles. The present application encompasses any of these methods.

In some embodiments, the individual has been diagnosed with or is suspected of having cancer. In some embodiments, the individual exhibits one or more symptoms associated with cancer. In some embodiments, the individual has a low tumor burden. In some embodiments, the individual is a human. In some embodiments, the individual is at least about any of 35, 40, 45, 50, 55, 60, 65, 70, 75, 80, or 85 years old. In some embodiments, the individual is no more than about any of 35, 30, 20, 15, 10, 5, or 1 year old. In some embodiments, the individual is a male. In some embodiments, the individual is a female. In some embodiments, the individual has a single lesion at presentation. In some embodiments, the individual has multiple lesions at presentation. In some embodiments, the individual has been previously treated for cancer. In some embodiments, the individual has not previously been treated for cancer.

The cancer described herein can be of any stage. In general, cancers can be evaluated according to Overall Stage Grouping, outlined as follows:

| | |
|---|---|
| Stage 0 | Carcinoma in situ |
| Stage I | Cancers are localized to one part of the body |
| Stage II | Cancers are locally advanced |
| Stage III | Cancers are also locally advanced. Whether a cancer is designated as Stage II or Stage III can depend on the specific type of cancer; for example, in Hodgkin's Disease, Stage II indicates affected lymph nodes on only one side of the diaphragm, whereas Stage III indicates affected lymph nodes above and below the diaphragm. The specific criteria for Stages II and III therefore differ according to diagnosis. |
| Stage IV | Cancers have often metastasized, or spread to other organs or throughout the body |

In some embodiments, the cancer is surgically treatable. In some embodiments, the cancer is not surgically treatable.

In some embodiments, the cancer is an early stage cancer, such as Stage 0. Stage I, or Stage II. In some embodiments, the cancer is a late stage cancer, such as Stage III or Stage IV. In some embodiments, the cancer is Stage III A. In some embodiments, the cancer is Stage IIIB or Stage IV. In some embodiments, the cancer is Stage IV.

In some embodiments, the cancer is early stage cancer, non-metastatic cancer, primary cancer, advanced cancer, locally advanced cancer, metastatic cancer, cancer in remission, or recurrent cancer. In some embodiments, the cancer is localized resectable, localized unresectable, or unresectable. In some embodiments, the cancer is a progressive cancer. In some embodiments, the cancer is substantially refractory to hormone therapy. In some embodiments, the cancer is HER2 positive. In some embodiments, the cancer is HER2 negative. In some embodiments, the cancer is estrogen receptor and/or progesterone receptor positive. In some embodiments, the cancer is estrogen receptor and/or progesterone receptor negative.

The methods provided herein can be practiced in an adjuvant setting. Alternatively, the methods can be practiced in a neoadjuvant setting, i.e., the method may be carried out before the primary/definitive therapy. In some embodiments, the method is a first, line therapy. In some embodiments, the method is a second line therapy.

The methods described herein can be useful for treating and providing beneficial effects to individuals having a cancer. In some embodiments, the cancer is a solid tumor. In some embodiments, the cancer is adenocarcinoma. In some embodiments, the cancer is sarcoma.

In some embodiments, the cancer is any one of the following: biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., glioblastoma, meningioma; glioma, e.g., astrocytoma, oligodendroglioma; medulloblastoma), cervical cancer (e.g., cervical adenocarcinoma), colorectal cancer (e.g., colon cancer, rectal cancer, colorectal adenocarcinoma), esophageal cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC)), kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leukemia (e.g., acute lymphoblastic leukemia (ALL), acute myeloid leukemia (AML), chronic myelogenous leukemia (CML), chronic lymphocytic leukemia (CLL)), lymphoma (e.g., Hodgkin lymphoma (HL), non-Hodgkin lymphoma (NHL), follicular lymphoma, diffuse large B-cell lymphoma (DLBCL), mantle cell lymphoma (MCL)), multiple myeloma (MM), myelodysplastic syndrome (MDS), myeloproliferative disorder (MPD) (e.g., polycythemia Vera (PV), essential thrombocythemia (ET), agnogenic myeloid metaplasia (AMM) a.k.a. primary myelofibrosis (PMF), chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), pancreatic cancer (e.g., pancreatic adenocarcinoma, intraductal papillary mucinous neoplasm (IPMN)), prostate cancer (e.g., prostate adenocarcinoma), skin cancer (e.g., squamous cell carcinoma (SCC), keratoacanthoma (KA), melanoma, basal cell carcinoma (BCC)) and soft tissue sarcoma (e.g., malignant fibrous histiocytoma (MFH), liposarcoma, malignant peripheral nerve sheath tumor (MPNST), chondrosarcoma, fibrosarcoma, rhabdomyosarcoma, myxosarcoma).

In some embodiments, the cancer is selected from the group consisting of bladder cancer, breast cancer, medulloblastoma, colorectal cancer, head and neck cancer, lung cancer (e.g., small cell lung cancer (SCLC), non-small cell lung cancer (NSCLC)), leukemia (e.g., acute lymphoblastic leukemia (ALL), acute myeloid leukemia (AML), chronic myelogenous leukemia (CML), chronic lymphocytic leukemia (CLL)), lymphoma (e.g., Hodgkin lymphoma (HL), non-Hodgkin lymphoma (NHL)), multiple myeloma (MM), chronic myeloproliferative disorder (primary myelofibrosis, polycythemia vera, essential thrombocythemia), osteosarcoma, ovarian cancer, pancreatic cancer, prostate cancer, basal cell carcinoma (BCC)) and chondrosarcoma.

In some embodiments, the cancer is a cancer that is difficult to treat. Examples of cancers that are difficult to treat include, but are not limited to, brain cancer (such as glioblastoma), liver cancer, lung cancer, ovarian cancer, pancreatic cancer, and skin cancer (such as melanoma).

In some embodiments, the cancer is a cancer that is or is known to be associated with cachexia. Examples of cancers that are associated with cachexia include, but are not limited to, gastric cancer, pancreatic cancer, lung, esophageal, colorectal, head and neck cancer, and hematological malignancies.

In some embodiments, the cancer is liver cancer, such as hepatocarcinoma ("HCC"), hepatoblastoma, cholangiocarcinoma, angiosarcoma, hemangiosarcoma, or lymphoma of the liver. In some embodiments, the liver cancer (such as HCC) is early stage, non-metastatic, primary, advanced, locally advanced, metastatic, liver cancer (such as HCC) in remission, or recurrent liver cancer (such as recurrent HCC). In some embodiments, the liver cancer (such as HCC) is localized resectable (i.e., tumors that are confined to a portion of the liver that allows for complete surgical removal), localized unresectable (i.e., the localized tumors may be unresectable because crucial blood vessel structures are involved or because the liver is impaired), or unresectable (i.e., the tumors involve till lobes of the liver and/or has spread to involve other organs (e.g., lung, lymph nodes, bone). In some embodiments, the liver cancer (such as HCC) is, according to TNM classifications, a stage I tumor (single tumor without vascular invasion), a stage II tumor (single tumor with vascular invasion, or multiple tumors, none greater than 5 cm), a stage III tumor (multiple tumors, any greater than 5 cm, or tumors involving major branch of portal or hepatic veins), a stage IV tumor (tumors with direct invasion of adjacent organs other than the gallbladder, or perforation of visceral peritoneum), N1 tumor (regional lymph node metastasis), or M1 tumor (distant metastasis). In some embodiments, the liver cancer (such as HCC) is, according to AJCC (American Joint Commission on Cancer) staging criteria, stage T1, T2, T3, or T4 HCC. In some embodiments, the liver cancer is any one of liver cell carcinomas, fibrolamellar variants of HCC, and mixed hepatocellular cholangiocarcinomas.

In some embodiments, the individual is of Asian ancestry. In some embodiments, the individual is HBsAg positive. In some embodiments, the individual is HBsAg negative. In some embodiments, the individual has underlying liver cirrhosis, in some embodiments, the individual does not have the underlying liver cirrhosis. In some of embodiments, the individual is genetically or otherwise predisposed (e.g., having a risk factor) to developing liver cancer (such as HCC). These risk factors include, but are not limited to, age, sex, race, diet, history of previous disease, presence of precursor disease (e.g., hepatitis B or hepatitis C viral infection, liver cirrhosis), genetic (e.g., hereditary) considerations, and environmental exposure. In some embodiments, the individuals at risk for liver cancer (such as HCC) include, e.g., those having relatives who have experienced liver cancer (such as HCC), and those whose risk is determined by analysis of genetic or biochemical markers.

Thus, for example, in some embodiments, there is provided a method of treating liver cancer (such as HCC) in an individual having liver cancer (such as HCC), comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of treating liver cancer (such as HCC) in an individual having liver cancer (such as HCC), comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of treating liver cancer (such as HCC) in an individual having liver cancer (such as HCC), comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, there is provided a method of prolonging survival of an individual having liver cancer (such as HCC), comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of prolonging survival in an individual having liver cancer (such as HCC), comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of prolonging survival of an individual having liver cancer (such as HCC), comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia. In some embodiments, the method prolongs the survival of the individual by at least any of 1, 2, 3, 4, 5, 6, 7, 8, 9, 10, 11, 12, 18, or 24 months.

In some embodiments, there is provided a method of preventing body weight loss of an individual having liver cancer (such as HCC), comprising administering to the individual an effective amount of a composition comprising oxprenolol or a pharmaceutically acceptable salt thereof, wherein the composition is enantiomerically enriched for S-oxprenolol (for example comprising an enantiomeric excess of about 99% of S-oxprenolol). In some embodiments, there is provided a method of preventing (or delaying) development of cancer cachexia in an individual having liver cancer (such as HCC), comprising administering to the individual an effective amount of a composition comprising oxprenolol or a pharmaceutically acceptable salt thereof, wherein the composition is enantiomerically enriched for S-oxprenolol (for example comprising an enantiomeric excess of about 99% of S-oxprenolol). In some embodiments, there is provided a method of preventing loss of lean body mass in an individual having liver cancer (such as HCC), comprising administering to the individual an effective amount of a composition comprising oxprenolol or a pharmaceutically acceptable salt thereof, wherein the composition is enantiomerically enriched for S-oxprenolol (for example comprising an enantiomeric excess of about 99% of S-oxprenolol). In some embodiments, there is provided a method of preventing loss of body fat in an individual having liver cancer (such as HCC), comprising administering to the individual an effective amount of a composition comprising oxprenolol or a pharmaceutically acceptable salt thereof, wherein the composition is enantiomerically enriched for S-oxprenolol (for example comprising an enantiomeric excess of about 99% of S-oxprenolol). In some embodiments, the individual has no symptom of cancer cachexia. In some embodiments, the individual has one or more symptoms of cancer cachexia.

In some embodiments, there is provided a method of alleviating one or more symptoms associated with liver cancer (such as HCC) in an individual, comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of alleviating one or more symptoms associated with liver cancer (such as HCC) in an individual, comprising administering to the individual an effective amount of a composition comprising oxprenolol or a pharmaceutically acceptable salt thereof, wherein the composition comprises an enantiomeric excess of at least about 99%; (for example at least about 99.9%) of S-oxprenolol. In some embodiments, there is provided a method of alleviating one or more symptoms associated with liver cancer (such as HCC) in an individual, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99%; of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, there is provided a method of prolonging progression-free survival in an individual with liver cancer (such as HCC), comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, there is provided a method of prolonging progression-free survival in an individual with liver cancer (such as HCC), comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of prolonging progression-free survival in an individual with liver cancer (such as HCC), comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, there is provided a method of treating muscle wasting in an individual having liver cancer (such as HCC), comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, a method of treating muscle wasting in an individual having liver cancer (such as HCC), comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, a method of treating muscle wasting in an individual having liver cancer (such as HCC), comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia, in some embodiments, the method leads to a reduction of muscle wasting, i.e., a slow-down of muscle loss. In some embodiments, the method leads to a reversal of muscle wasting, i.e., an increase in muscle weight.

In some embodiments, there is provided a method of improving quality of life in an individual having liver cancer (such as HCC), comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, a method of improving quality of life in an individual having liver cancer (such as HCC), comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, a method of improving quality of life in an individual having liver cancer (such as HCC), comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, there is provided a method of increasing food intake of an individual having liver cancer (such as HCC), comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, a method of increasing food intake of an individual having liver cancer (such as HCC), comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, a method of increasing food intake of an individual having liver cancer (such as HCC), comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, there is provided a method of increasing locomotive activity of an individual having liver cancer (such as HCC), comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about, any one of 20%, 30%, 40%, 50%, 60%, 70%, 80%, 90%, 95%, 96%, 97%, 98%, or 99%) of S-oxprenolol. In some embodiments, a method of increasing locomotive activity of an individual having liver cancer (such as HCC), comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, a method of increasing locomotive activity of an individual having liver cancer (such as HCC), comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, there is provided a method of improving fatigue or dyspnea in of an individual having liver cancer (such as HCC), comprising administering to the individual an effective amount of a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, a method of improving fatigue or dyspnea in of an individual having liver cancer (such as HCC), comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, a method of improving fatigue or dyspnea in of an individual having liver cancer (such as HCC), comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the individual has no symptom of cancer cachexia. In some embodiments, the individual has one or more symptoms of cancer cachexia.

In some embodiments, the individual being treated is no more than about 18 years old. For example, in some embodiments, there is provided a method of treating a cancer in an individual having pediatric cancer, comprising administering to the individual an effective amount of a composition comprising oxprenolol or a pharmaceutically acceptable salt thereof, wherein the composition is enantiomerically enriched for S-oxprenolol, wherein the individual is no more than about 18 years old. In some embodiments, there is provided a method of promoting growth in an individual having a cancer, wherein the individual is no more than about 18 years old. In some embodiments, there is provided a method of preventing loss of growth in an individual having cancer, wherein the individual is no more than about 18 years old. In some embodiments, there is provided a method of treating muscle wasting in an individual having cancer, wherein the individual is no more than about 18 years old. In some embodiments, there is provided a method of prolonging survival of an individual having cancer, wherein the individual is no more than about 18 years old. In some embodiments, there is provided a method of improving quality of life in an individual having cancer, wherein the individual is no more than about 18 years old. In some embodiments, the individual is no more than about any of 17, 16, 15, 14, 13, 12, 11, 10, 9, 8, 7, 6, 5, 4, 3, 2, or 1 year old. In some embodiments, the individual is about 9 to about 15 years old. In some embodiments, the individual is about 5 to about 9 years old. In some embodiments, the individual is about 1 to about 5 years old. In some embodiments, the individual is no more than about 1 year old, such as about 6 months old to about 1 year old, less than about 6 months old, or less than about 3 months old. In some embodiments, the composition comprises a composition comprising oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, or 99%) of S-oxprenolol. In some embodiments, the composition comprises an enantiomeric excess of at least about 99% (for example at least about 99.9%) of S-oxprenolol.

In some embodiments, the individual no more than about 18 years old for the methods described herein has a solid tumor. In some embodiments, the solid tumor is sarcoma. In some embodiments, the solid tumor is carcinoma (such as adenocarcinoma). In some embodiments, the solid tumor is a neuroendocrine tumor. In some embodiments, the solid tumor is a cancer of the connective tissue. In some embodiments, the solid tumor is a cancer arising from mesenchymal cells (e.g., skeletal muscle progenitor cells). In some embodiments, the solid tumor is a soft tissue tumor (such as soft tissue sarcoma). In some embodiments, the solid tumor is selected from the group consisting of neuroblastoma, rhabdomyosarcoma, osteosarcoma, retinoblastoma, CNS tumor, Wilm's tumor, and Ewing's sarcoma. In some embodiments, the solid tumor is an abdominal tumor, a soft tissue tumor, a bone tumor, or an eye tumor. In some embodiments, the solid tumor is a brain tumor. In some embodiments, the solid tumor is melanoma. In some embodiments, the solid tumor is a soft tissue sarcoma, such as rhabdomyosarcoma. In some embodiments, the solid tumor is neuroblastoma. In some embodiments, the solid tumor is osteosarcoma. In some embodiments, the solid tumor is retinoblastoma. In some embodiments, the solid tumor is a heritable retinoblastoma.

In some embodiments, the individual no more than about 18 years old for the methods described herein has a central nervous system (CNS) tumor, such as an astrocytoma, a brain stem glioma, an ependymoma, a germ cell tumor, or a medulloblastoma. Childhood central nervous system tumors do not typically spread outside the brain and spinal cord. In some embodiments, the CNS tumor is a recurrent CNS tumor.

In some embodiments, the individual no more than 18 years old for the methods described herein has Wilms' tumor (also known as nephroblastoma). In some embodiments, the individual has Stage I Wilms' tumor. In some embodiments, the individual has Stage II Wilms' tumor. In some embodiments, the individual has Stage III Wilms' tumor. In some embodiments, the individual has Stage IV Wilms' tumor. In some embodiments, the individual has Stage V Wilms' tumor. In some embodiments, the individual has recurrent Wilms' tumor.

In some embodiments, the individual no more than 18 years old for the methods described herein has soft tissue sarcoma. In some embodiments, the individual has Stage I soft tissue sarcoma. In some embodiments, the individual has Stage II soft tissue sarcoma. In some embodiments, the individual has Stage III soft tissue sarcoma. In some embodiments, the individual has Stage IV soft tissue sarcoma. In some embodiments, the individual has recurrent soft tissue sarcoma.

In some embodiments, the individual no more than about 18 years old for the methods described herein has Ewing's sarcoma. In some embodiments, the individual has localized Ewing's sarcoma. In some embodiments, the individual has metastatic Ewing's sarcoma. In some embodiments, the individual has Stage 1 Ewing's sarcoma, hr some embodiments, the individual has Stage 2 Ewing's sarcoma. In some embodiments, the individual has Stage 3 Ewing's sarcoma. In some embodiments, the individual has Stage 4 Ewing's sarcoma. In some embodiments, the individual has recurrent Ewing's sarcoma.

In some embodiments, the individual no more than about 18 years old for tire methods described herein has hepatoblastoma.

In some embodiments, the individual no more than about 18 years old for the methods described herein has a haematological disease, such as leukemia (for example acute leukemia).

Enantiomerically Enriched Oxprenolol Compositions

The methods described herein comprise administration of compositions comprising oxprenolol or a pharmaceutically acceptable salt thereof, w-herein the composition is enantiomerically enriched for S-oxprenolol (for example comprising an enantiomeric excess of at least about 99% of S-oxprenolol). The present disclosure also provides such compositions which are useful for the methods disclosed herein.

Oxprenolol is 1-[2-(allyloxy)phenoxy]-3-(isopropylamino)propan-2-ol. The structure of oxprenolol is shown below.

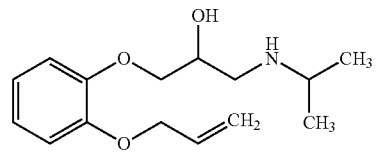 [SMILES: C=CCOc1ccccc1OCC(O)CNC(C)C]

Oxprenolol exists in optically active forms. Optically active compounds have the ability to rotate the plane of plane-polarized light. In describing an optically active compound, the prefixes R and S are used to denote the absolute configuration of the molecule about its chiral center(s). The prefixes "d" and "l" or (+) and (−) are employed to designate the sign of rotation of plane-polarized light by the compound, with (−) or l meaning that the compound is "levorotatory" and with (+) or d meaning that the compound is "dextrorotatory." There is no correlation between nomenclature for the absolute stereochemistry and for the rotation of an enantiomer. For a given chemical structure, these compounds, called "stereoisomers," are identical except that they are mirror images of one another. A specific stereoisomer can also be referred to as an "enantiomer," and a mixture of such isomers is often called an "enantiomeric" or "racemic" mixture.

Oxprenolol is a chiral compound. As a racemic mixture, there is a mixture of (R)-(+)-oxprenolol and (S)-(−)-oxprenolol. Analytical methods, such as HPLC, can be used for separation and quantification of (R)-(+)-oxprenolol and (S)-(−)-oxprenolol in mixtures. The structures of (R)-(+)-oxprenolol and (S)-(−)-oxprenolol are shown below.

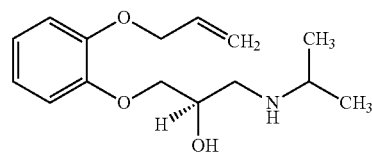

(R)-(+)-oxprenolol or R-oxprenolol
(R)-1-(2-(allyloxy)phenoxy)-3-(isopropylamino)propan-2-ol

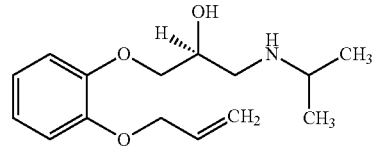

(S)-(−)-oxprenolol or S-oxprenolol
(S)-1-(2-(allyloxy)phenoxy)-3-(isopropylamino)propan-2-ol The compositions described herein are enantiomerically enriched for S-oxprenolol. For example, in some embodiments, the composition comprises an enantiomeric excess of at least about 1%, 5%, 10%, 15%, 20%, 25%, 30%, 35%, 40%, 45%, 50%, 55%, 60%, 65%, 70%, 75%, 80%, 85%, 90% or 95% of S-oxprenolol. In some embodiments, the composition comprises an enantiomeric excess of at least about 90%, 91%, 92%, 93%, 94%, 95%, 96%, 97%, 98%, or 99% of S-oxprenolol. In some embodiments, the composition comprises an enantiomeric excess of at least about 90%, 95%, 98%, 99%, or 100%, up to the detectable limit of purity, of S-oxprenolol. In some embodiments, the composition comprises an enantiomeric excess of any of about 1-4%, 5-9%, 10-11%, 20-29%, 30-39%, 40-49%, 50-59%, 60-69%, 70-79%, 80-89%, 90-99, or 100% of S-oxprenolol. In some embodiments, the composition comprises an enantiomeric excess of at least about 99% or 100% of S-oxprenolol (i.e., pure S-oxprenolol). In some embodiments, the composition comprises an enantiomeric excess of at least 99.1, 99.2, 99.3, 99.4, 99.5, 99.6, 99.7, 99.8, 99.9 or 100% of S-oxprenolol (i.e., pure S-oxprenolol). Methods of making enantiomerically enriched compositions of oxprenolol are known in the art.

Two main routes are established for obtaining enantiomerically enriched compounds: (1) asymmetric syntheses and (2) racemic resolutions. (R. A. Sheldon: *The Industrial Synthesis of Optically Active Compounds*, in Miklós Simonyi (editor), *Problems and Wonders if Chiral Molecules*, Akadémiai Kiadó, Budapest, 1990, S. 349-386). The syntheses give medium-high yields and excellent enantiomeric excess, but the resolutions are limited by 50% yield. Both technologies involve techniques such as dynamic kinetic resolution (DKR) and membrane-based extraction (Augustian J et al., Process Biochemistry Volume 45, Issue 10, October 2010, Pages 1587-1604). One method describes enantiomer enrichment of oxprenolol up to 68% enantiomeric excess was achieved by using a cellulose tris(3,5-dimethylphenylcarbamate) (CTPC)-coated rayon-belt. (Yashima E. et al., Tetrahedron: Asymmetry Volume 6, Issue 8, August 1995, Pages 1889-1890).

The compositions described herein in some embodiments are present in pharmaceutical compositions. The pharmaceutical compositions may further comprise one or more pharmaceutically acceptable carrier (or excipients). A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In some embodiments, the pharmaceutical composition is sterile.

Also provided here are unit dosage forms comprising a pharmaceutical compositions described herein. These unit dosage forms can be stored in a suitable packaging in single or multiple unit dosages and may also be further sterilized and sealed. Unit dosage forms can be provided, for example, in the form of tablets, capsules, vials, and any other forms described herein.

In some embodiments, there is provided a composition (such as a pharmaceutical composition, for example a unit dosage) comprising oxprenolol or a pharmaceutically acceptable salt thereof, wherein the composition is enantiomerically enriched for S-oxprenolol (for example comprising an enantiomeric excess of at least about 99% of S-oxprenolol), wherein the amount of S-oxprenolol in the composition (such as pharmaceutical composition) is included in any of the following ranges: about 5 to about 10 mg, about 10 to about 20 mg, about 20 to about 30 mg, about 30 to about 40 mg, about 40 to about 50 mg, about 50 to about 60 mg, about 60 to about 70 mg, about 70 to about 80 mg, about 80 to about 90 mg, about 90 to about 100 mg, about 100 to about 110 mg, about 110 to about 120 mg, about 120 to about 130 mg, about 130 to about 140 mg, about 140 to about 150 mg, about 150 to about 160 mg. In some embodiments, the amount of S-oxprenolol in the composition is about 20 to about 160 mg, including for example about 50 to about 150 mg, 80 to about 150 mg, about 90 to about 140 mg, about 100 to about 120 mg. In some embodiments, the composition is suitable for oral administration.

In some embodiments, the composition is provided in a slow release form. For example, oxprenolol can be administered in slow release form. (Eur J Drug Metab Pharmacokinet. 1998 April-June; 23(2): 178-84; Bennett P N, Bennett J, Bradbrook I, Francis J, John V A, Rogers H, Turner P, Warrington S J. Br J Clin Pharmacol. 1985:19 Suppl 2:171S-175S; and Woods K L, Jack D B, Kendall M J, Halsey A, O'Donnell M L, Warrington S J, John V A. Br J Clin Pharmacol. 1985; 19 Suppl 2:177S-184S.)

Also provided are articles of manufacture comprising the compositions, formulations, and unit dosages described herein in suitable packaging for use in the methods of treatment, methods of administration, and dosage regimens described herein. Suitable packaging for compositions described herein are known in the art, and include, for example, vial (such as sealed vials), vessels (such as sealed vessels), ampules, bottles, jars, flexible packaging (e.g., sealed Mylar or plastic bags), and the like. These articles of manufacture may further be sterilized and/or sealed.

Dosages and Administration Route

The dosage of the compositions described herein administered to an individual (such as a human) may vary with the particular composition, the method of administration, and the particular stage of cancer. The amount should be sufficient to produce a desirable response, such as a therapeutic or prophylactic response against cancer. In some embodiments, the amount of the composition is a therapeutically effective amount, hr some embodiments, that amount of the composition is a prophylactically effective amount. In some embodiments, the amount of total oxprenolol in the composition is below the level that induces a toxicological effect (i.e., an effect above a clinically acceptable level of toxicity) or is at a level where a potential side effect can be controlled or tolerated when the composition is administered to the individual.

In some embodiments, the amount of S-oxprenolol in the composition is included in any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg. In some embodiments, the amount of S-oxprenolol in the composition is included in any of the following ranges: about 5 to about 10 mg, about 10 to about 20 mg, about 20 to about 30 mg, about 30 to about 40 mg, about 40 to about 50 mg, about 50 to about 60 mg, about 60 to about 70 mg, about 70 to about 80 mg, about 80 to about 90 mg, about 90 to about 100 mg, about 100 to about 110 mg, about 110 to about 120 mg, about 120 to about 130 mg, about 130 to about 140 mg, about 140 to about 150 mg, about 150 to about 160 mg. In some embodiments, the amount of S-oxprenolol in the composition is about 20 to about 160 mg, including for example about 50 to about 150 mg, 80 to about 150 mg, about 90 to about 140 mg, about 100 to about 120 mg.

In some embodiments, the amount of S-oxprenolol in the composition includes at least about any of 0.1 mg/kg, 0.5 mg/kg, 1 mg/kg, 2.5 mg/kg, 5 mg/kg, 7.5 mg/kg, 10 mg/kg, 15 mg/kg, or 20 mg/kg. In some embodiments, the amount of S-oxprenolol in the composition includes less than about any of 35 mg/kg, 30 mg/kg, 25 mg/kg, 20 mg/kg, 15 mg/kg, 10 mg/kg, 5 mg/kg, 2.5 mg/kg, 2 mg/kg, 1 mg/kg, 0.5 mg/kg, or 0.1 mg/kg.

Exemplary dosing frequencies include, but are not limited to, weekly without break; weekly, three out of four weeks; once every three weeks; once every two weeks; weekly, two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week. In some embodiments, the composition is administered daily. In some embodiments, the composition is administered twice daily. In some embodiments, the composition is administered at least once (such as at least any of 2×, 3×, or 4×) daily.

The administration of the composition can be extended over an extended period of time, such as from about a month up to about seven years or life-long. In some embodiments, the composition is administered over a period of at least about any of 2, 3, 4, 5, 6, 7, 8, 9, 10, 11, 12, 18, 24, 30, 36, 48, 60, 72, or 84 months or life-long. In some embodiments, the composition is administered over a period of at least one month, wherein the interval between each administration is no more than about a week.

The compositions described herein can be administered to an individual (such as human) via various routes, including, for example, intravenous, intra-arterial, intraperitoneal, intraportal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used.

Once improvement of the patient's disease has occurred, the dose may be adjusted for preventative or maintenance treatment. For example, the dosage or the frequency of administration, or both, may be reduced as a function of the symptoms, to a level al which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Pharmaceutical Formulations and Administration

The pharmaceutical compositions described herein may be formulated as solutions, emulsions, suspensions, dispersions, or inclusion complexes such as cyclodextrins in suitable pharmaceutical solvents or earners, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. Preferably, the compositions are formulated for intravenous or oral administration.

For oral administration, the compositions may be provided in a solid form, such as a tablet or capsule, or as a solution, emulsion, or suspension. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating. The oral formulations may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (eg sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the compositions may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Formulations suitable for parenteral including intravenous administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

Drug Combinations

The methods of the embodiments comprise administering an effective amount of at least one compound of the embodiments; optionally the compound may be administered in combination with one or more additional therapeutic agents, particularly therapeutic agents known to be useful for treating a cancer afflicting the subject.

The additional active ingredients may be administered in a separate pharmaceutical composition from a compound of the embodiments or may be included with a compound of the embodiments in a single pharmaceutical composition. The additional active ingredients may be administered simultaneously with, prior to, or after administration of a compound of the embodiments.

In certain embodiments, the additional therapeutic agent is selected from the group consisting of progestins, corticosteroids, metoclopramide, cannabinoids, thalidomide, melatonin, clenbuterol, anabolic steroids, omega 3 fatty acids, NSAIDs, beta-blocking agents, 5HT-modulating agents, SARMs, ghrelin, growth hormone, IGF-1, myostatin antibody, activin receptor antagonist, and agents which inhibit the renin-angiotensin systems (such as renin inhibitor, ACE inhibitors, and angiotensin receptor antagonists).

Kits

The present application also provides kits, medicines, compositions, and unit dosage forms for use in any of the methods described herein.

Kits provided herein include one or more containers comprising any one of the compositions described herein and/or other agent(s), and in some embodiments, further comprise instructions for use in accordance with any of the methods described herein. The kit may further comprise a description of selection of individual suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a) a composition comprising oxprenolol or a pharmaceutically acceptable salt thereof and a pharmaceutically acceptable carrier, wherein the composition is enantiomerically enriched for S-oxprenolol, and b) instructions for administering the composition for treatment of cancer (such as liver cancer).

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of S-oxprenolol as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the pharmaceutical compositions and instructions for use and packaged in quantities sufficient for storage and use in pharmacies, for example, hospital pharmacies and compounding pharmacies.

Also provided are medicines, compositions, and unit dosage forms useful for the methods described herein. For example, the present disclosure provides, in some embodiments, a composition comprising S-oxprenolol for treating cancer in an individual having cancer. The present disclosure provides, in some embodiments, a composition comprising S-oxprenolol for prolonging survival of an individual having cancer. The present disclosure provides, in some embodiments, a composition comprising S-oxprenolol for preventing body weight loss of an individual having cancer.

For example, the present disclosure provides, in some embodiments, a composition comprising S-oxprenolol for the manufacture of a medicament for treating cancer in an individual having cancer. The present disclosure provides, in some embodiments, a composition comprising S-oxprenolol for the manufacture of a medicament for prolonging survival of an individual having cancer. The present disclosure provides, in some embodiments, a composition comprising S-oxprenolol for the manufacture of a medicament for preventing body weight loss of an individual having cancer.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1. Synthesis of S-Oxprenolol

The synthesis of S-oxprenolol is shown in Scheme 1.

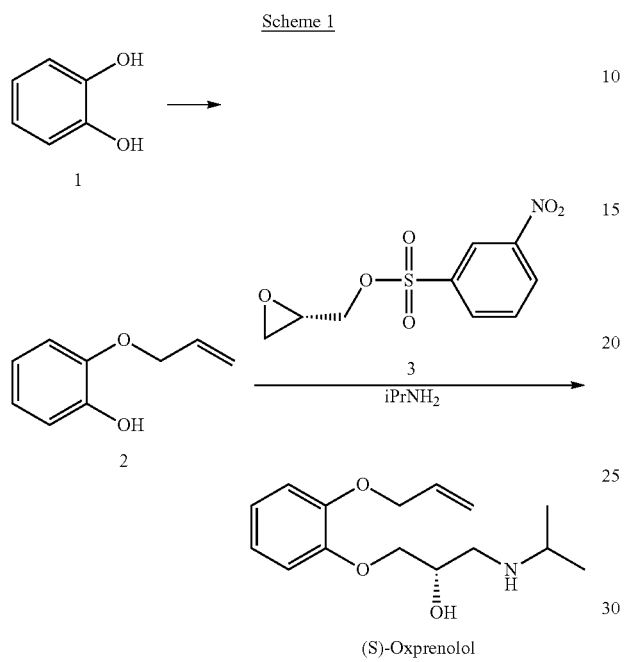

Preparation of 2-(allyloxy)phenol

To a solution of catechol (1) (40.0 g, 0.364 mol) in acetone (160 mL) was added potassium carbonate (50.0 g, 0.363 mol) portion-wise at room temperature, over a period of 30 minutes. After the addition was complete the mixture was stirred at room temperature for 1 hour. Allyl bromide (31.0 mL, 0.358 mol) was then added over a period of 30 minutes, and the reaction heated to 60-70° C. for 6 hours. The reaction was allowed to cool, then water and ethyl acetate were added and the mixture was separated. The organic layer was dried (MgSO$_4$) and the solvent evaporated to give 2-(allyloxy)phenol, (2) (46.2 g) as a 7:3 mixture of mono and bis alkylated material.

$^1$H NMR (300 MHz, CDCl$_3$) δ 6.93-6.77 (m, 4H), 6.05 (m, 1H), 5.41 (dd, 1H), 5.30 (m, 1H), 4.61 (d, 2H). LCMS: Rt 0.70 min, [M+H]$^+$ 148.9, 70%.

Preparation of S-oxprenolol

CsF (22.8 g, 0.150 mol) was added to a solution of 2-(allyloxy)phenol (7.50 g, 0.050 mol) in DMF (100 mL) and stirred for 1 hour at room temperature. (S)-Glycidyl nosylate (13.0 g, 0.050 mol) was added and the reaction stirred for 72 hours at room temperature, then added dropwise to $^i$PrNH$_2$ (97 mL, 1.26 mol) and stirred overnight. The reaction mixture was diluted with EtOAc (150 mL) and water (200 mL) and the solids removed by filtration. The phases were separated and the organic layer washed with water (100 mL), then brine (100 mL), dried over MgSO$_4$ and concentrated. Purification by column chromatography (5-10% MeOH/DCM then 5% (17% NH$_3$/MeOH) in DCM) gave (S)-oxprenolol (4.67 g, 20%) as a brown solid.

$^1$H NMR (300 MHz, CDCl$_3$) δ 6.92-6.89 (m, 2H), 6.82-6.79 (m, 2H), 5.99 (m, 1H), 5.37 (d, 1H), 5.21 (d, 1H), 4.87 (br s, 1H), 4.51 (d, 2H), 3.85 (d, 2H), 3.80 (m, 1H), 2.69-2.61 (m, 2H), 2.47 (m, 1H), 1.48 (br s, 1H), 0.93 (d, 6H).

LCMS: Rt 1.78 min, [M+H]$^+$ 266.1, 100%.

Example 2. Synthesis of R-Oxprenolol

The synthesis of S-oxprenolol is shown in Scheme 2.

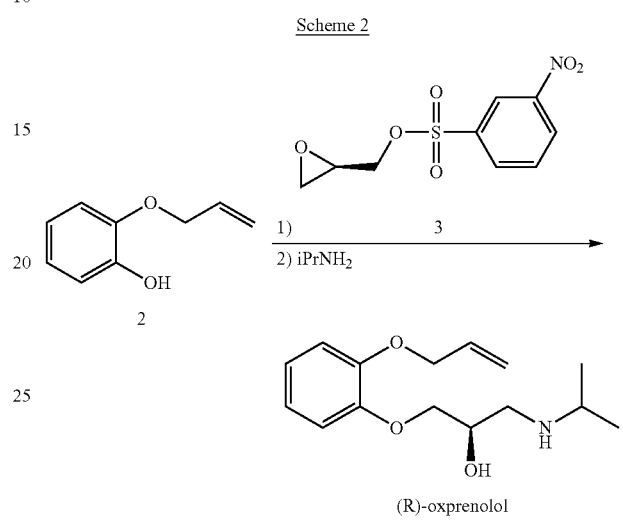

Preparation of R-oxprenolol

CsF (2.95 g, 19.4 mmol) and K$_2$CO$_3$ (17.3 g, 125 mmol) were added to a solution of 2-(allyloxy)phenol (14.4 g, 96.2 mmol) in DMF (250 mL) and stirred for 30 minutes at room temperature. (R)-Glycidyl nosylate (25.0 g, 96.4 mmol) was added and the reaction stirred for 48 hours at room temperature. $^i$PrNH$_2$ (190 mL, 2.21 mol) was added in one portion and the reaction stirred for 72 hours. The reaction mixture was diluted with water (1.0 L) and extracted with EtOAc (3×300 mL). The combined organics were washed with HCl (2.0 M, 3×300 mL). The aqueous layer was pH adjusted to pH 12 with NaOH (2.0 M) and extracted into EtOAc (2×500 mL). This was washed with 1:1 water/brine (3×500 mL), then with brine (500 mL), dried over Na$_2$SO$_4$ and concentrated. The crude solid was triturated from heptanes, filtered and dried under vacuum at 40° C. overnight to give (R)-oxprenolol (24.5 g, 69%) as a brown solid.

$^1$H NMR (300 MHz, CDCl$_3$) δ 6.92-6.89 (m, 2H), 6.82-6.79 (m, 2H), 5.99 (m, 1H), 5.37 (d, 1H), 5.21 (d, 1H), 4.87 (br s, 1H), 4.51 (d, 2H), 3.85 (d, 2H), 3.80 (m, 1H), 2.69-2.61 (m, 2H), 2.47 (m, 1H), 1.48 (br s, 1H), 0.93 (d, 6H).

LCMS: Rt 1.79 min, [M+H]$^+$ 266.1, 99%.

Example 3. Study Protocol with Yoshida Hepatoma Model

Ascites hepatoma Yoshida AH-130 cells (10$^8$ cells) were inoculated into about 200 gram male Wistar nits by i.p. injection. Alternatively animals received saline injection only (sham). The day after inoculation animals were randomized into various groups and then received twice daily treatment with either placebo or various test compositions by oral gavage over a period of up to 17 days. The primary endpoints of the study included assessment of body weight, body composition (with and without tumor), and survival.

Body composition was monitored by NMR. Echocardiography was used in instances to monitor condition of the heart. Organ weight was assessed at the end of the study (or after death) as a secondary endpoint. In addition, locomotor activity and food intake were also assessed. FIG. 1 provides a diagram showing the design study. R- and S-oxprenolol were manufactured to order by Peakdale Molecular, Peakdale Science Park, Sheffield Road, Chapel-en-le-Frith, High Peak SK23 0PG, UK

Example 4. Effect of S-Oxprenolol or R-Oxprenolol on Survival

Figure 2:
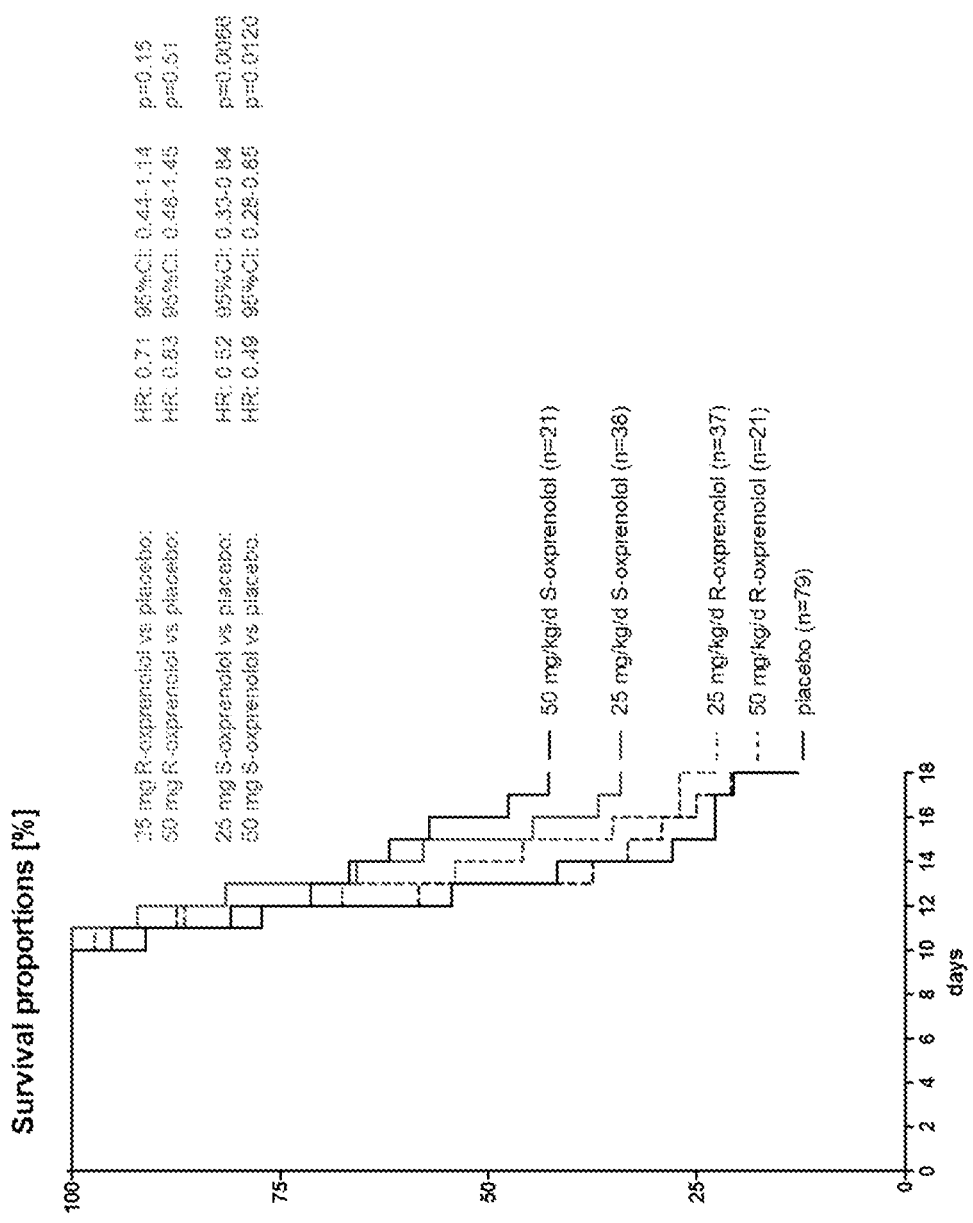
FIG. 2 is a graph showing the percent survival of rat populations that were administered with S-oxprenolol or R-oxprenolol. The sample size in the population is indicated by "n." "HR" refers to hazard ratio. "CI" refers to confidence interval. "95% CI" is 95% confidence interval, "p" refers to p-value.

To study the effect of S-oxprenolol and R-oxprenolol on survival, survival was monitored over time. FIG. 2 shows the percent survival of rats that were administered with S-oxprenolol or R-oxprenolol at dosages of 25 mg/kg/day or 50 mg/kg/day. As shown in FIG. 2, rats receiving S-oxprenolol had longer survival than those in the placebo group or those receiving R-oxprenolol. Rats receiving R-oxprenolol did not show statistically significant improvement on survival over those in the placebo group.

Figure 3:
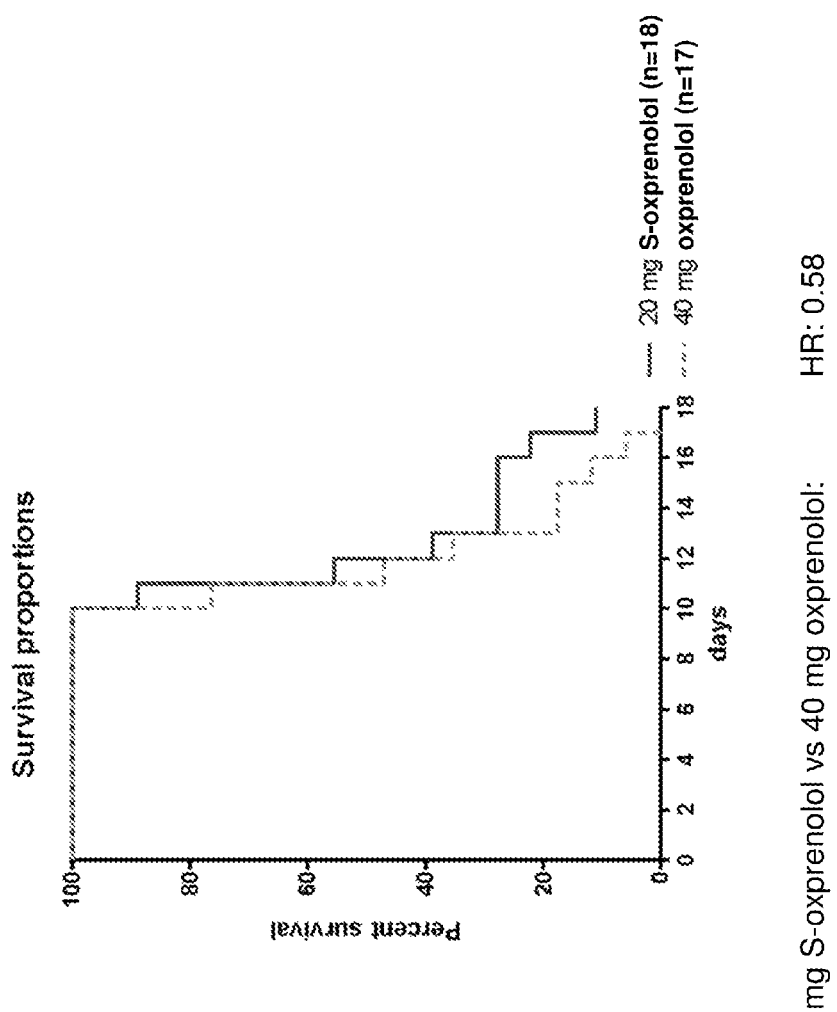
FIG. 3 is a graph showing the percent survival of rat populations that were administered with S-oxprenolol or a racemic mixture of oxprenolol. The sample size in the population is indicated by "n." "HR" refers to hazard ratio. "CI" refers to confidence interval. "95% CI" is 95% confidence interval.

FIG. 3 shows the percent survival of rats that were administered with S-oxprenolol or a racemic mixture of oxprenolol at dosages of 20 mg/kg/day and 40 mg/kg/day respectively. Because the racemic mixture contains 50% of S-oxprenolol and 50% of R oxprenolol, the effective amount of S-oxprenolol in each composition was the same. As shown in FIG. 3, rats receiving S-oxprenolol had longer survival than those receiving the racemic mixture, even though the effective amount of S-oxprenolol in each composition was the same.

Figure 4:
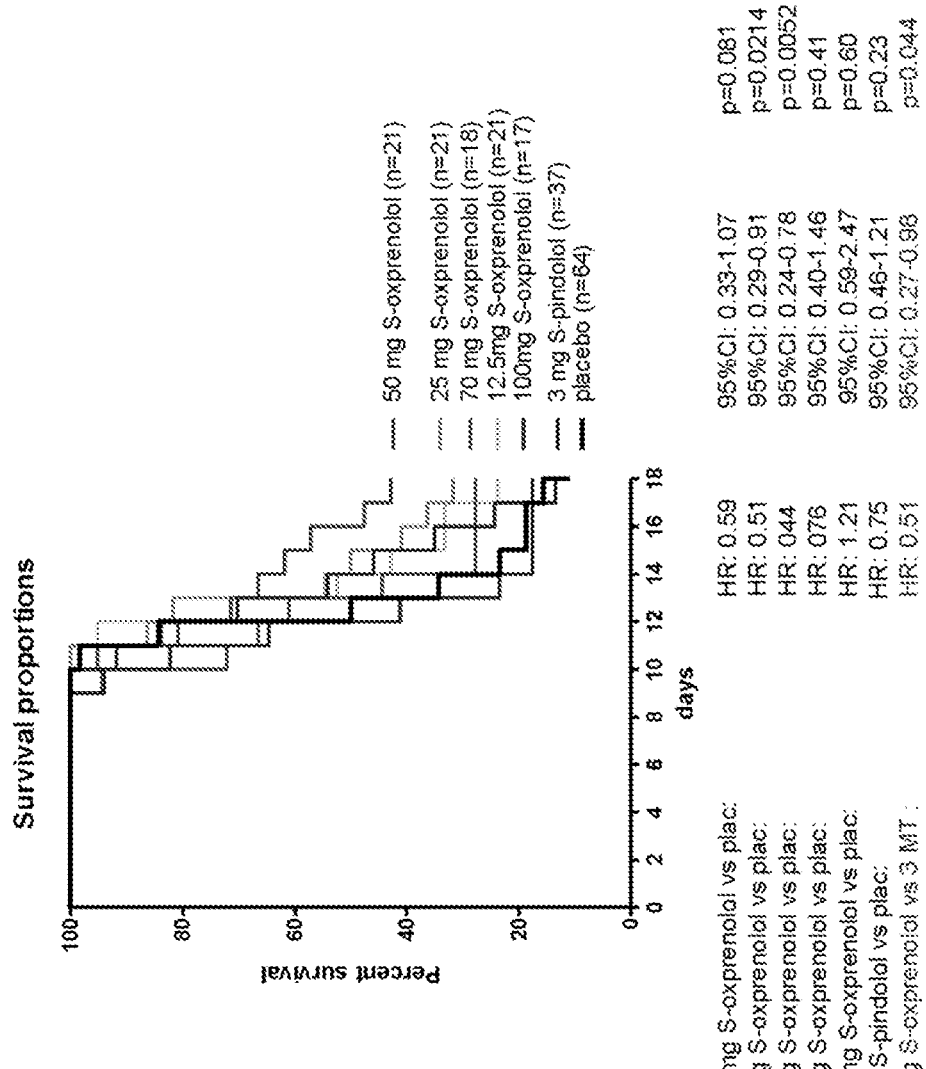
FIG. 4 is a graph showing the percent survival of rat populations that were administered various dosages of the S-oxprenolol. Comparison to placebo (plac) and S-pindolol was also provided. The sample size in the population is indicated by "n." "HR" refers to hazard ratio. "CI" refers to confidence interval. "95% CI" is 95% confidence interval, "p" refers to p-value.
Figure 5:
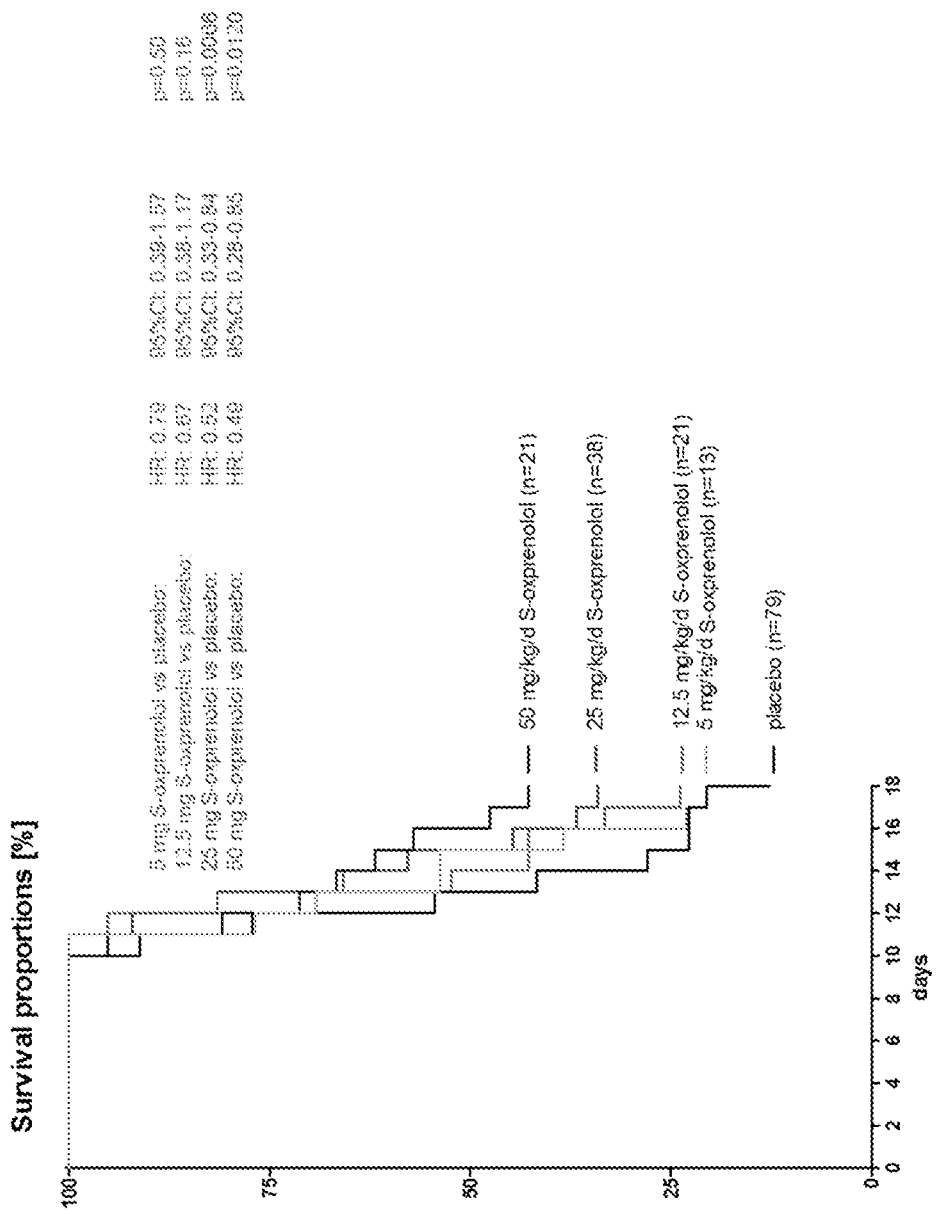
FIG. 5 is a graph showing the percent survival of rat populations that were administered with various dosages of the S-oxprenolol. The sample size in the population is indicated by "n." "HR" refers to hazard ratio. "CI" refers to confidence interval. "95% CI" is 95% confidence interval, "p" refers to p-value.

FIG. 4 show's the percent survival of rats that were administered with S-oxprenolol at dosages of 12.5, 25, 50, 70, or 100 mg/kg/day. One control group received S-pindolol at its preferred dosage of 3 mg/kg/day. FIG. 5 further show's the percent survival of rats that were administered with S-oxprenolol at dosages of 5, 12.5, 25, or 50 mg/kg/day. As shown in both FIGS. 4 and 5, 50 mg/kg/day S-oxprenolol had the best effect on survival among all dosages tested. Furthermore, as shown in FIG. 4, S-oxprenolol was significantly superior to either placebo or S-pindolol at its preferred dose.

Figure 6:
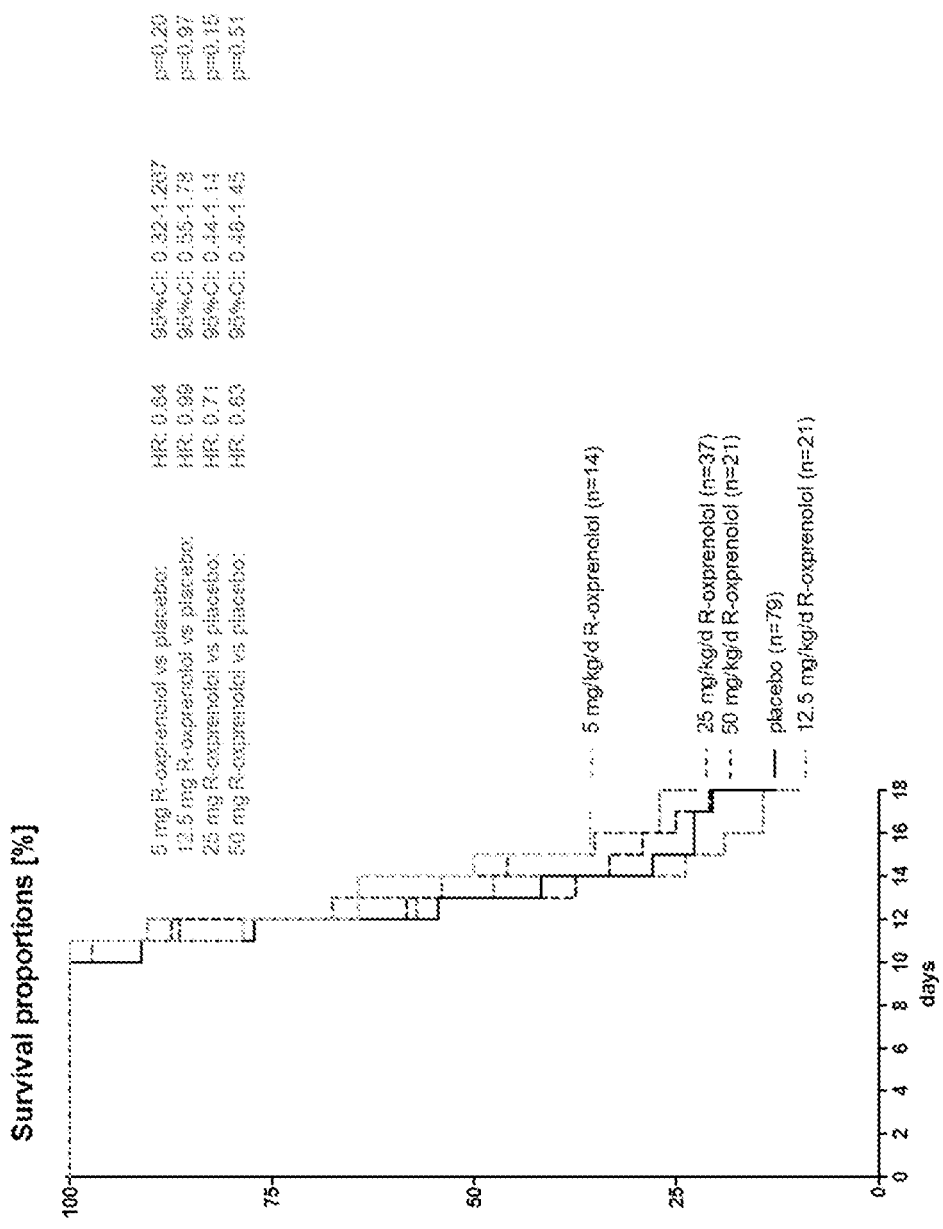
FIG. 6 is a graph showing the percent survival of rat populations that were administered with various dosages of the R-oxprenolol. The sample size in the population is indicated by "n." "HR" refers to hazard ratio. "CI" refers to confidence interval. "95% CI" is 95% confidence interval, "p" refers to p-value.

FIG. 6 shows the percent survival of rats that were administered with R-oxprenolol at dosages of 5, 12.5, 25, or 50 mg/kg/day. As shown in FIG. 6, no statistically significant survival benefit over placebo was observed in rats administered with R-oxprenolol.

Example 5. Effect of S-Oxprenolol or R-Oxprenolol on Body Weight

To study the effect of the test compounds on body weight, body weight was monitored over time. The sham body weight was 71.6±1.8 g.

Figure 7:
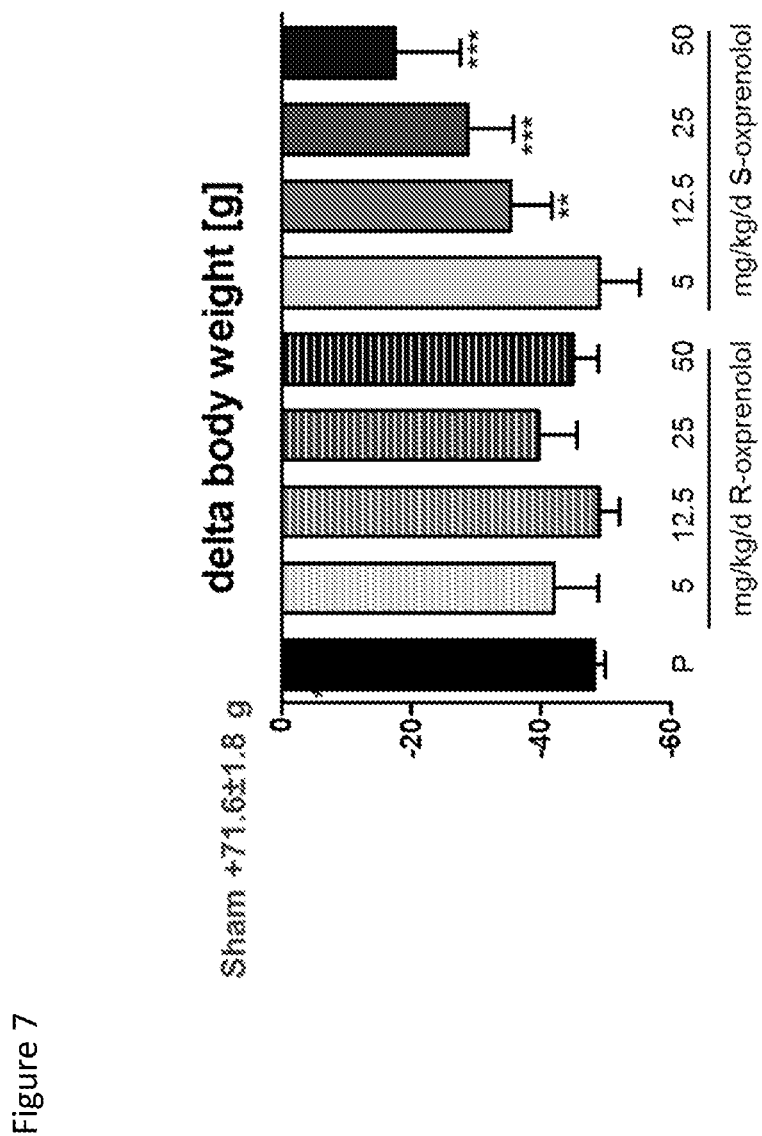
FIG. 7 is a graph showing the change in body weight (in grams ("g")) of rat populations that were administered with S-oxprenolol or R-oxprenolol. Comparison to placebo (P) was also provided. The two asterisks () indicate p<0.01. The three asterisks (*) indicate p<0.001.

FIG. 7 show's the change of body weight (in grams) in rats administered with S-oxprenolol or R-oxprenolol at dosage of 5, 12.5, 25, or 50 mg/kg/day. As shown in FIG. 7, rats receiving S-oxprenolol had less body weight loss than those in the placebo group and those administered with R-oxprenolol.

Figure 8:
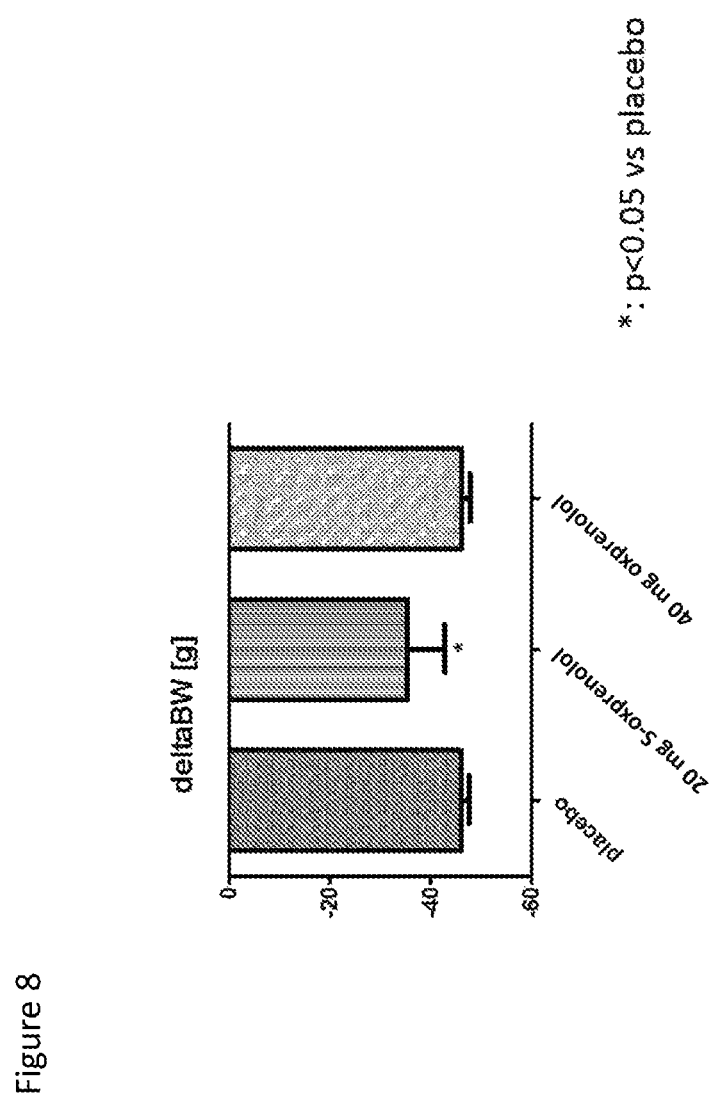
FIG. 8 is a graph showing the change in body weight (in grams ("g")) of rat populations that were administered with S-oxprenolol or a racemic mixture of oxprenolol. The asterisk (*) indicates that the p value is less than 0.05 versus the placebo.

FIG. 8 show's the change in body weight (in grams) of rat populations that were administered with S-oxprenolol or a racemic mixture of oxprenolol at dosages of 20 mg/kg/day and 40 mg/kg/day respectively. Because the racemic mixture contains 50% of S-oxprenolol and 50% of R-oxprenolol, the effective amount of S-oxprenolol in each composition was the same. As shown in FIG. 8, rats receiving S-oxprenolol had less body weight loss than those receiving the racemic mixture, even though the effective amount of S-oxprenolol in each composition was the same.

Figure 9:
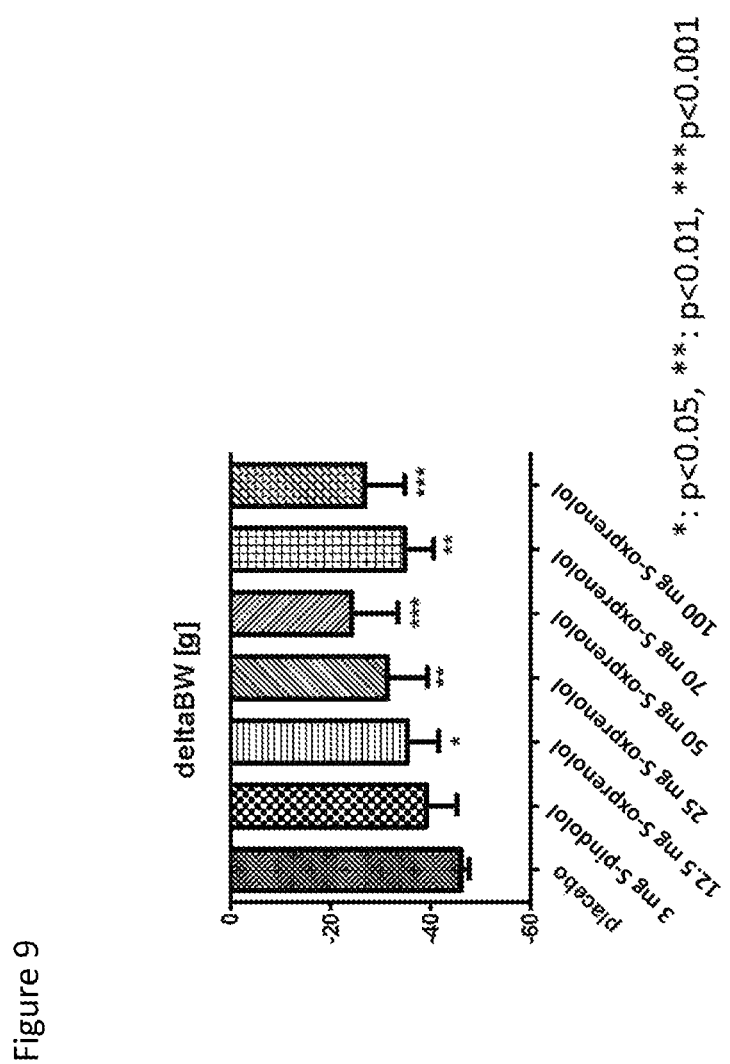
FIG. 9 is a graph showing the change in body weight (in grams ("g")) of rat populations that were administered with various dosages of the S-oxprenolol. Comparison to placebo and S-pindolol was also provided. The asterisk (*) indicates that the p value is less than 0.05. The two asterisks () indicate that the p value is less than 0.01. The three asterisks (*) indicate that the p value is less than 0.001.

FIG. 9 shows the change in body weight (in grams) of rats that were administered with S-oxprenolol at dosages of 12.5, 25, 50, 70, or 100 mg/kg/day. As shown in FIG. 9, rats receiving 50 mg/kg/day or 100 mg/kg/day of the S-oxprenolol had the least body weight loss.

Example 6. Effects of S-Oxprenolol or R-Oxprenolol on Preserving Lean Body Mass To study the effect of the test compounds on lean body mass, lean mass was determined at the end of the study. The sham lean body mass was 48.6±1.5 grams.

Figure 10:
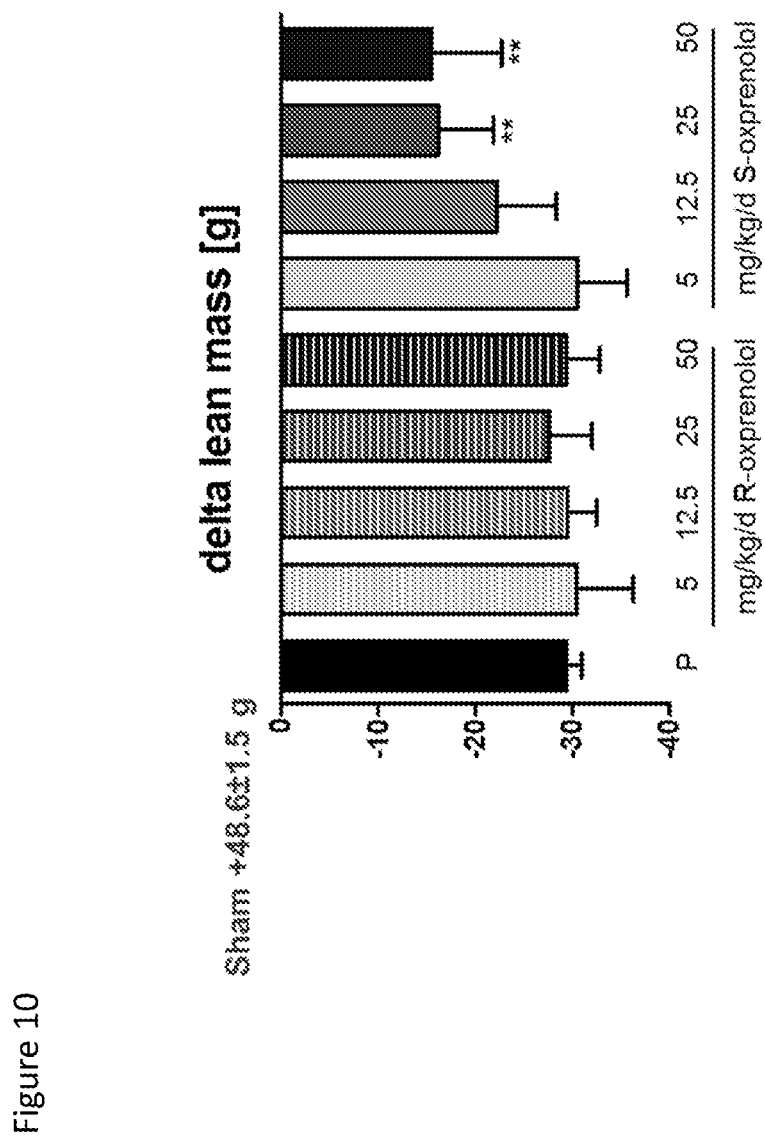
FIG. 10 is a graph showing the change in lean body mass (in grams ("g")) of rat populations that were administered with various dosages of the S-oxprenolol or R-oxprenolol. Comparison to placebo (P) was also provided. The asterisk (*) indicates P<0.05 versus placebo. The two asterisks (**) indicate P<0.01 versus placebo.

FIG. 10 shows the change in lean body mass (in grams) of rats that were administered with S-oxprenolol or R-oxprenolol at dosages of 5, 12.5, 25, or 50 mg/kg/day. As shown in FIG. 10, rats receiving S-oxprenolol at doses of 12.5 mg/kg/day or higher had less change in lean body mass than those receiving R-oxprenolol.

Figure 11B:
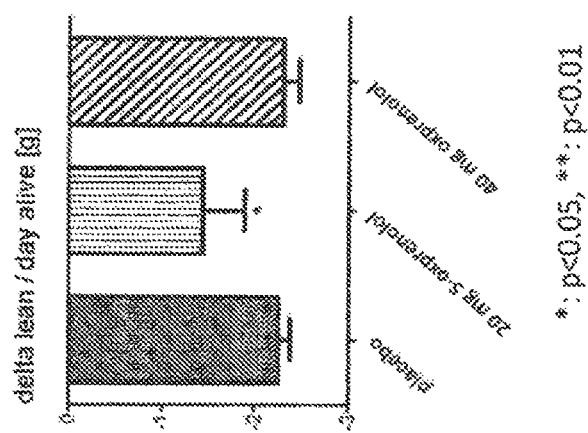
FIG. 11B is a graph showing the change in lean body mass (in grams ("g")) of rat populations that were administered with S-oxprenolol or a racemic mixture of oxprenolol that includes the factor of days alive. The asterisk (*) indicates that the p value is less than 0.05. The two asterisks (**) indicate that the p value is less than 0.01.
Figure 11A:
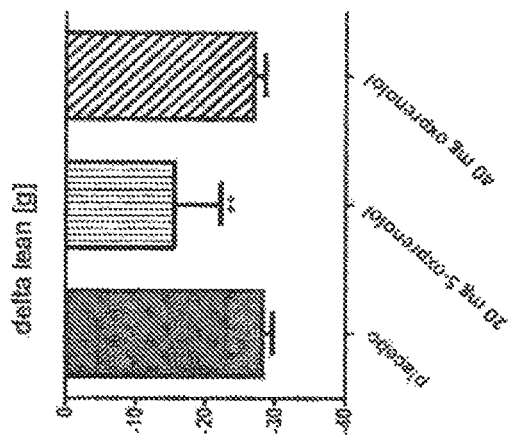
FIG. 11A is a graph showing the change in lean body mass (in grams ("g")) of rat populations that were administered with S-oxprenolol or a racemic mixture of oxprenolol.

FIG. 11A shows the change in lean body mass (in grams) of rats that were administered with S-oxprenolol or a racemic mixture of oxprenolol at dosages of 20 mg/kg/day and 40 mg/kg/day respectively. Because the racemic mixture contains 50% of S-oxprenolol and 50% of R-oxprenolol, the effective amount of S-oxprenolol in each composition was the same. As shown in FIG. 11A, rats receiving S-oxprenolol had less change in lean body weight than those receiving the racemic mixture, even though the effective amount of S-oxprenolol in each composition was the same.

To take into account the fact that more lean body mass loss is observed in rats that live longer, the results in FIG. 11A was further shown in FIG. 11B in terms of lean body weight mass/days alive. As shown in FIG. 11B, even after taking the days alive into account, rats receiving S-oxprenolol had less change in lean body mass than those receiving the racemic mixture.

Figure 12A:
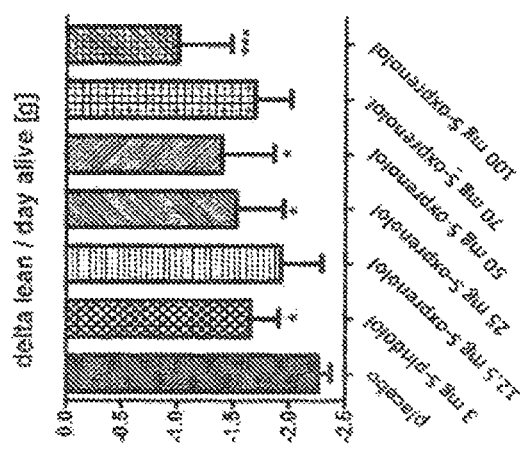
FIG. 12A is a graph showing the change in lean body mass fin grams ("g")) of rat populations that were administered with various dosages of the S-oxprenolol, S-pindolol, or placebo.
Figure 12B:
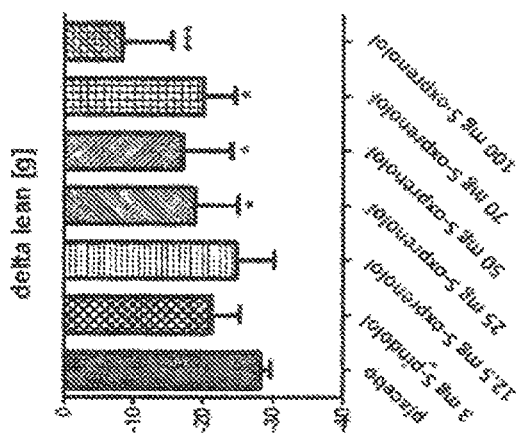
FIG. 12B is a graph showing the change in lean body mass (in grams ("g")) of rat populations that were administered with S-oxprenolol, S-pindolol, or placebo that includes the factor of days alive. The asterisk (*) indicates that the p value is less than 0.05 versus placebo. The three asterisks (***) indicate that the p value is less than 0.001 versus placebo.

FIG. 12A shows the change in lean body mass (in grams) of rats administered with S-oxprenolol at dosages of 12.5, 25, 50, 70, or 100 mg/kg/day. One control group received S-pindolol at its preferred dosage of 3 mg/kg/day. As shown in FIG. 12A, rats receiving 100 mg/kg/day of S-oxprenolol had the least change in lean body mass compared to rats receiving other doses S-oxprenolol. To take into account the fact that more lean body mass loss is observed in rats that live longer, the results in FIG. 12A was further shown in FIG. 12B in terms of lean body weight mass/days alive. As shown in FIG. 12B, rats receiving 100 mg/kg/day of S-oxprenolol had the least change in lean body mass/days alive compared to rats receiving other doses S-oxprenolol.

Example 7. Effects of S-Oxprenolol and R-Oxprenolol on Skeletal Muscle Atrophy and Heart Weight To study the effect of the test compounds on skeletal muscle atrophy and heart weight, the skeletal muscle mass and heart weight were determined at the end of the study.

Figure 13A:
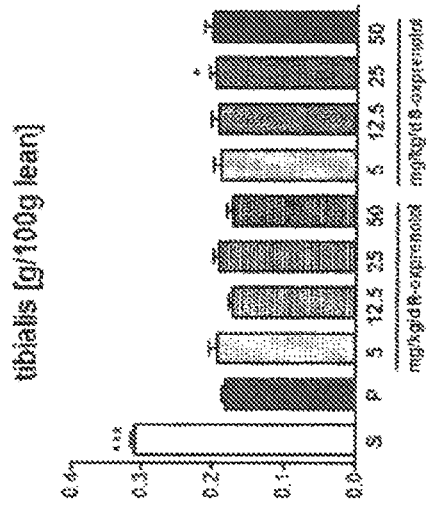
FIG. 13A is a graph showing the mass of gastrocnemius muscle (in grams per 100 grams of lean muscle mass ("g/100 g lean")) in rat populations that were administered with various dosages of S-oxprenolol or R-oxprenolol at the endpoint of the study.
Figure 13B:
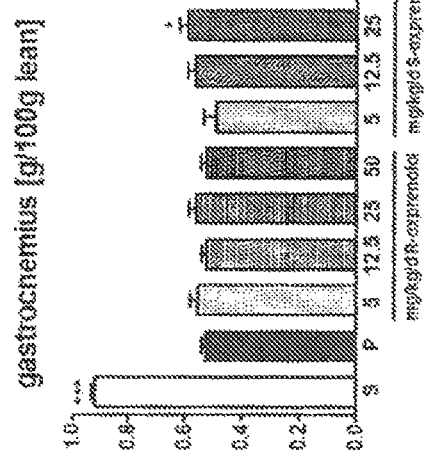
FIG. 13B is a graph showing the mass of tibialis anterior muscle (in grams per 100 grams of lean muscle mass ("g/100 g lean")) in rat populations that were administered with various dosages of S-oxprenolol or R-oxprenolol at the endpoint of the study.

FIGS. 13A-13D show the mass of various types of skeletal muscle (in grams/100 grams lean muscle) of rat populations that were administered with S-oxprenolol or R-oxprenolol at the dosages of 5, 12.5, 25, or 50 mg/kg/day. FIG. 13A shows results for gastrocnemius muscle. FIG. 13B shows results for tibialis anterior muscle. FIG. 13C shows results for soleus muscle. FIG. 13D shows results for extensor digitorum longus (EDL) muscle. FIGS. 13A-13D show that S-oxprenolol reduces wasting of individual hind limb muscles independent of their composition of slow and fast twitch muscle fibers (mixed fiber type: gastrocnemius and tibialis; slow fiber type: soleus; fast fiber type: EDL). R-oxprenolol does not have this protective effect. A higher muscle mass is associated with better muscle function.

Example 8. Effects of S-Oxprenolol and R-Oxprenolol on Preserving Fat Mass

To study the effect of the test compounds on fat mass, the fat mass were determined at the end of the study.

Figure 14:
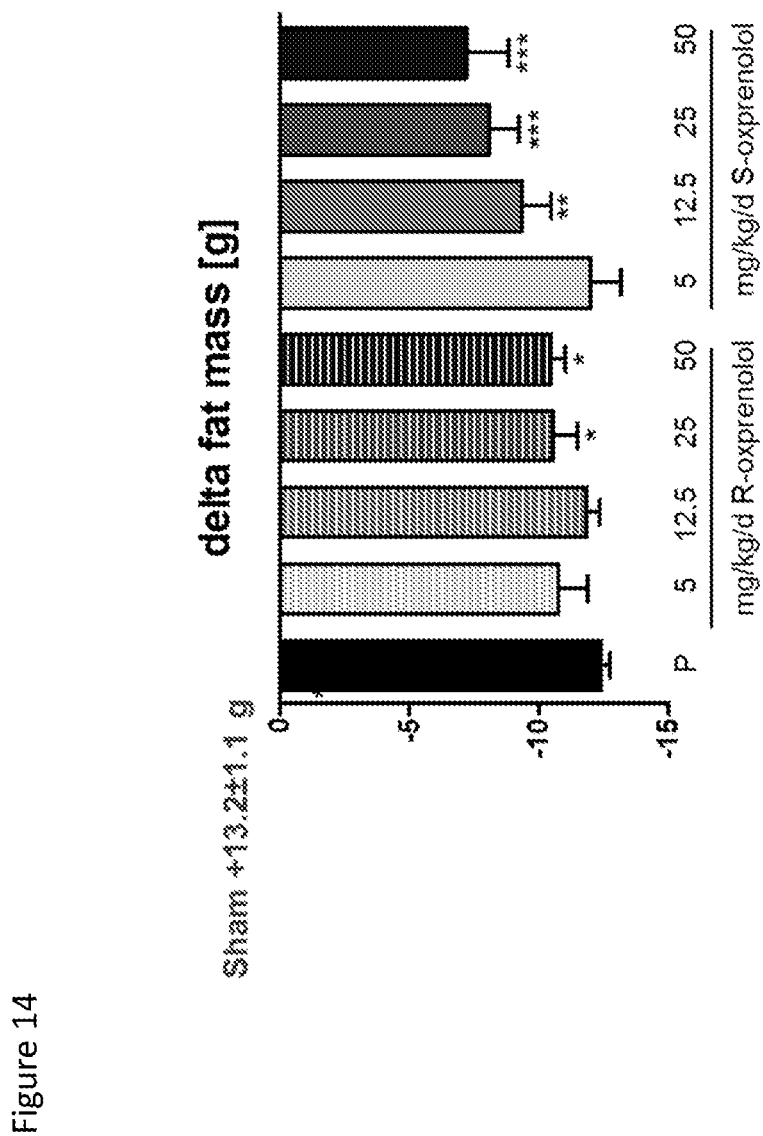
FIG. 14 is a graph showing the change in fat mass (in grams ("g")) of rat populations that were administered with S-oxprenolol or R-oxprenolol. Comparison to placebo (P) was also provided. The asterisk (*) indicates p<0.05 versus placebo. The two asterisks () indicate p<0.01 versus placebo. The three asterisks (*) indicate p<0.001 versus placebo.

FIG. 14 shows the change in fat mass (in grams) of rats administered with S-oxprenolol or R-oxprenolol at dosages of 5, 12.5, 25, or 50 mg/kg/day. As shown in FIG. 14, rats receiving S-oxprenolol at 12.5 mg/kg/day or higher had less fat mass loss than those in the placebo group or those receiving R-oxprenolol.

Figure 15A:
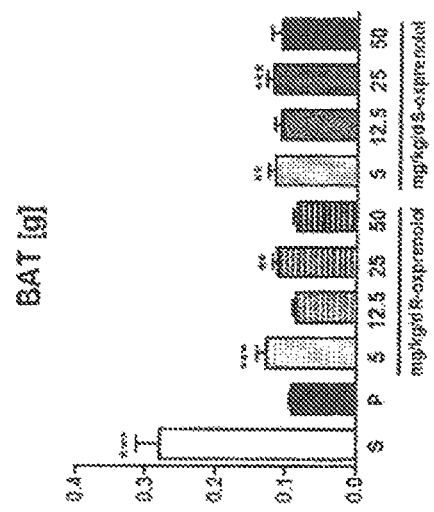
FIG. 15A is a graph showing the weight of white adipose tissue (WAT) (in grams ("g")) of rat populations that were administered with various dosages of the S-oxprenolol or R-oxprenolol at the endpoint of the study.

FIG. 15A shows the weight of white adipose tissue (WAT) (in grams) of rats administered with S-oxprenolol or R-oxprenolol at dosages of 5, 12.5, 25, or 50 mg/kg/day. As shown in FIG. 15A, S-oxprenolol had better effects in reducing fat wasting than R-oxprenolol.

Figure 15B:
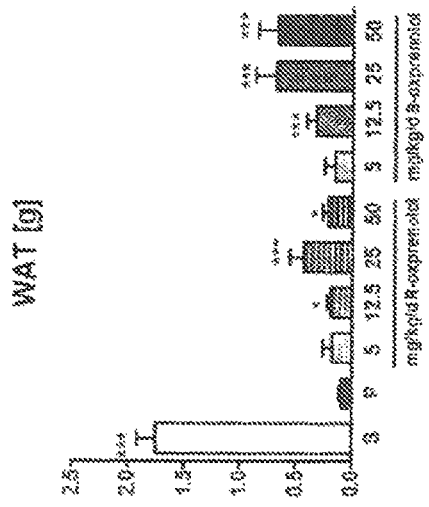
FIG. 15B is a graph showing the weight of brown adipose tissue (WAT) (in grams ("g")) of rat populations that were administered with various dosages of the S-oxprenolol or R-oxprenolol at the endpoint of the study. Comparison to placebo (P) and sham (S) was also provided. The asterisk (*) indicates p<0.05 versus placebo. The two asterisks () indicate p<0.01 versus placebo. The three asterisks (*) indicate p<0.001 versus placebo.

FIG. 15B shows the weight of brown adipose tissue (BAT) (in grams) of rats administered with S-oxprenolol or R-oxprenolol at dosages of 5, 12.5, 25, or 50 mg/kg/day. As shown in FIG. 15B, both enantiomers of oxprenolol protect BAT mass and thus treated rats retained better control of thermogenesis.

Figure 16A:
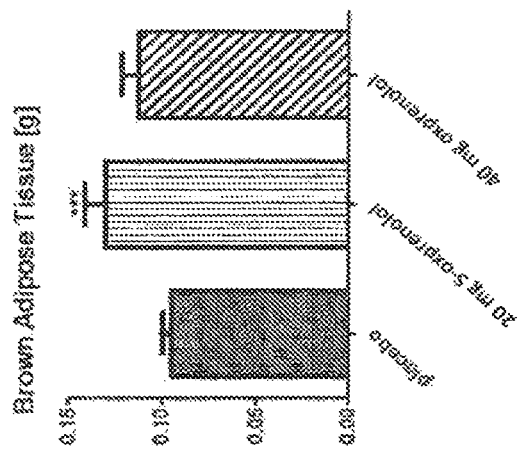
FIG. 16A is a graph showing the weight of white adipose tissue (WAT) (in grams ("g")) rat populations that were administered with S-oxprenolol or a racemic mixture of oxprenolol at the endpoint of the study.

FIG. 16A shows the weight of white adipose tissue (WAT) (in grams) of rats administered with S-oxprenolol or a racemic mixture of oxprenolol at dosages of 20 mg/kg/day or 40 mg/kg/day respectively. Because the racemic mixture contains 50% of S-oxprenolol and 50% of R-oxprenolol, the effective amount of S-oxprenolol in each composition was the same. As shown in FIG. 16A, rats receiving S-oxprenolol had significantly better effect in preserving the white adipose tissue than those receiving the racemic mixture, even though the even though the effective amount of S-oxprenolol in each composition was the same.

Figure 16B:
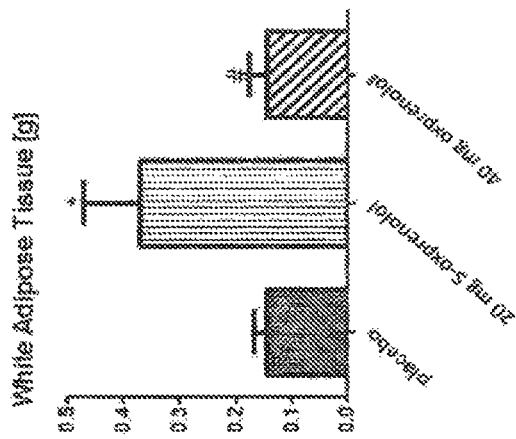
FIG. 16B is a graph showing the weight of brown adipose tissue (WAT) (in grams ("g")) rat populations that were administered with S-oxprenolol or a racemic mixture of oxprenolol at the endpoint of the study. The asterisk (*) indicates that the p value is less than 0.05 versus placebo. The three asterisks (***) indicate that the p value is less than 0.001 versus placebo. The pound sign (#) indicates that the p value is less than 0.05 versus 20 mg of S-oxprenolol.

FIG. 16B shows the weight of brown adipose tissue (BAT) (in grams) of rats administered with S-oxprenolol or a racemic mixture of oxprenolol at dosages of 20 mg/kg/day and 40 mg/kg/day respectively. Because the racemic mixture contains 50% of S-oxprenolol and 50% of R-oxprenolol, the effective amount of S-oxprenolol in each composition was the same. As shown in FIG. 16B, rats receiving S-oxprenolol had better effect in preserving the brown adipose tissue than those receiving the racemic mixture, even though the even though the effective amount of S-oxprenolol in each composition was the same.

Example 9. Effect of S-Oxprenolol or R-Oxprenolol on Quality of Life

To study the effect of the test compounds on quality of life, parameters of quality of life such as food intake and locomotor activity were assessed at Day 11.

Figure 17:
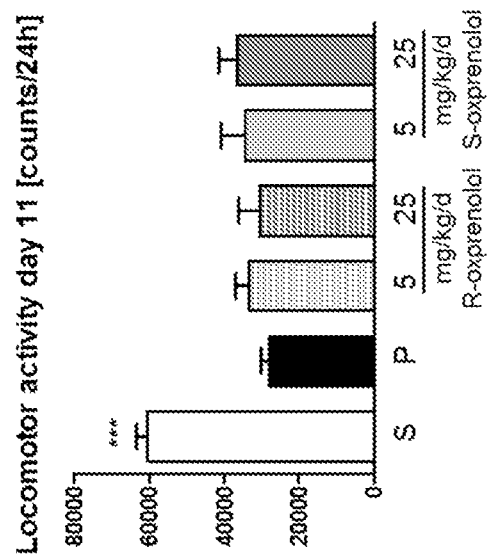
FIG. 17 is a graph showing the food intake (grams of food per 24 hours ("g/24 h")) of rat populations that were administered with various dosages of the S-oxprenolol or R-oxprenolol. Comparison to placebo (P) and sham (S) was also provided. The two asterisks () indicate p<0.001 versus placebo. The three asterisks (*) indicate p<0.001 versus placebo.

FIG. 17 show's food intake of rats administered with S-oxprenolol or R-oxprenolol at dosages of 5 mg/kg/day or 25 mg/kg/day. As shown in FIG. 17, rats receiving S-oxprenolol or R-oxprenolol had higher food intake than those in the placebo group. Rats receiving 25 mg/kg/day S-oxprenolol had higher food intake than those receiving the same amount of R-oxprenolol.

Figure 18:
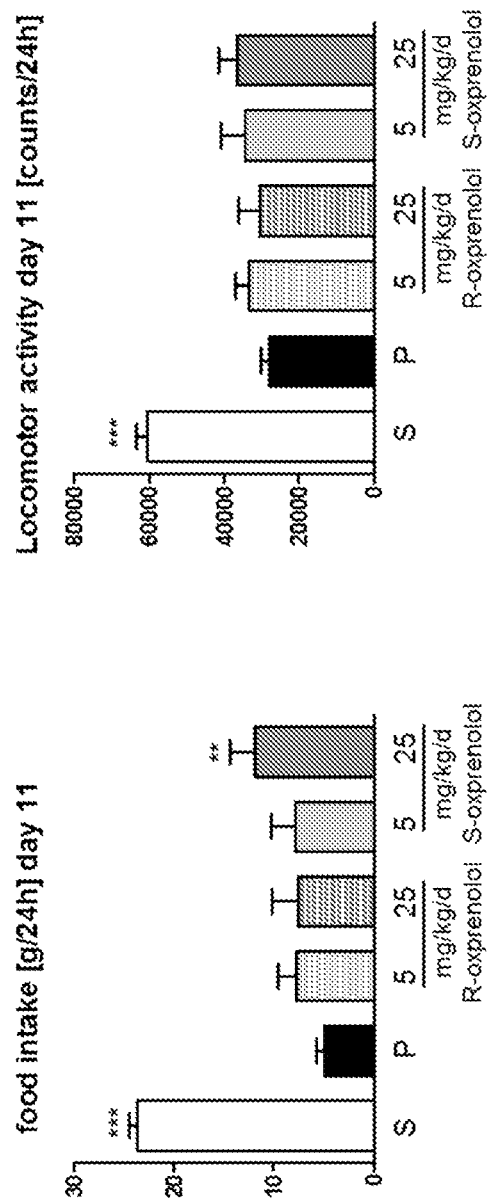
FIG. 18 is a graph showing the locomotor activity (counts per 24 hours ("counts/24 h")) of rat populations that were administered with various dosages of S-oxprenolol or R-oxprenolol. Comparison to placebo (P) and sham (S) was also provided. The three asterisks (***) indicate p<0.001 versus placebo.

FIG. 18 shows the locomotor activity of rats administered with the S-oxprenolol or R-oxprenolol at dosages of 5 mg/kg/day or 25 mg/kg/day. As shown in FIG. 18, rats receiving S-oxprenolol or R-oxprenolol had higher locomotive activity than those in the placebo group. Rats receiving 25 mg/kg/day S-oxprenolol had higher locomotive activity than those receiving the same amount of R-oxprenolol.

Example 10. Effect of S-Oxprenolol or R-Oxprenolol on Tumor Growth

To study the effect of the test compounds on tumor growth, tumor growth was assessed at tire end of the study.

Figure 19:
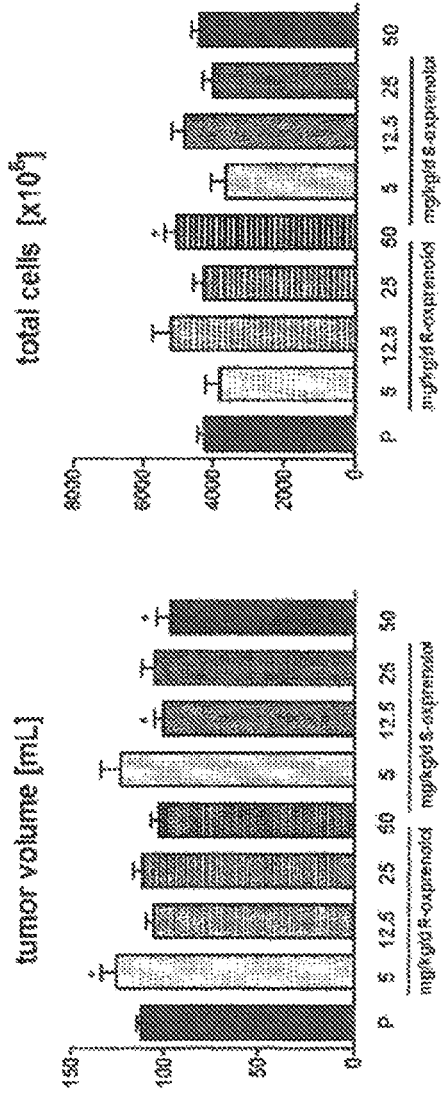
FIG. 19A is a graph showing the change in tumor volume (in mL) of rat populations that were administered with dosages of the S-oxprenolol or R-oxprenolol. Comparison to placebo (P) was also provided.
FIG. 19B is a graph showing the change in total cells in a tumor of rat populations that were administered with various dosages of the S-oxprenolol or R-oxprenolol. Comparison to placebo (P) was also provided. The asterisk (*) indicates p<0.05 versus placebo.

FIG. 19A shows the tumor volume (in ml) of rats administered with S-oxprenolol or R-oxprenolol at dosages of 5, 12.5, 25, or 50 mg/kg/day. FIG. 19B shows the total number of cells in a tumor of rats administered with S-oxprenolol or R-oxprenolol at dosages of 5, 12.5, 25, or 50 mg/kg/day. As shown in FIGS. 19A and 19B, rats receiving S-oxprenolol or R-oxprenolol did not have any significant effects on tumor growth compared to those in the placebo group.

Figure 20:
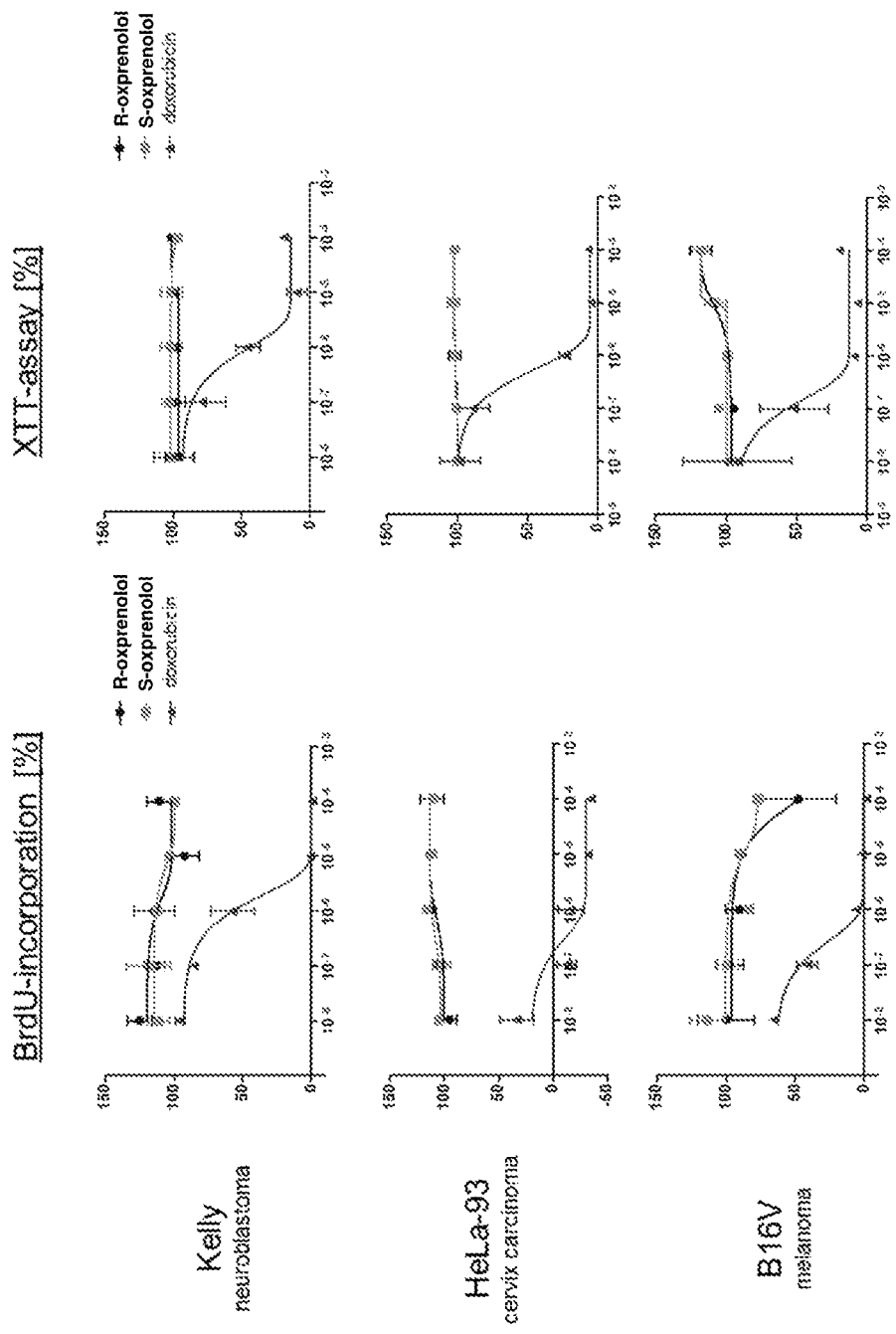
FIG. 20 is a graph showing effect of S-oxprenolol, R-oxprenolol, or doxorubicin on tumor growth, as assessed by BrdU incorporation and XTT assay with various tumor cells, namely, Kelly (neuroblastoma), Hela-93 (cervix carcinoma), and B16V (melanoma).

The effect of the test compounds on tumor growth was also evaluated in an in vitro experiment with various tumor cells, namely, Kelly (neuroblastoma), Hela-93 (cervix carcinoma), and B16V (melanoma). Cell growth was assessed by BrdU incorporation (left of FIG. 20) and XTT assay (right of FIG. 20). Doxorubicin was used as a positive control. As shown in FIG. 20, neither S-oxprenolol nor R-oxprenolol showed any inhibitor effects on tumor cell proliferation.

Example 11. Effects of Racemic Mixture of S-Oxprenolol and R-Oxprenolol

The test compounds as mixtures of enantiomers in certain percentages were tested on a population of rats.

Figure 21:
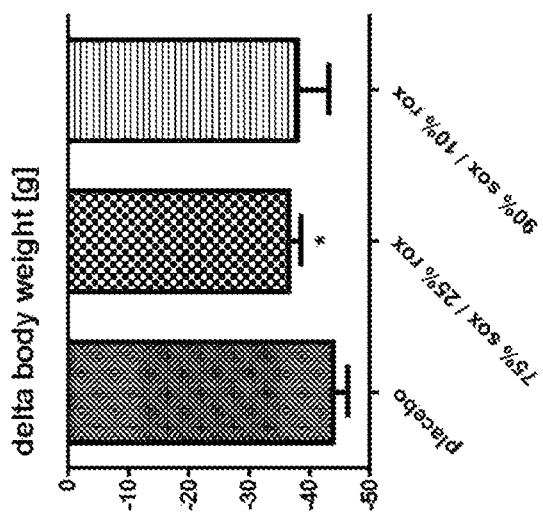
FIG. 21 is a graph showing the change in body weight (in grams ("g")) of rat populations that were administered with 75% S-oxprenolol (sox)/25% R-oxprenolol (rox); 90% S-oxprenolol (sox)/10% R-oxprenolol (rox); or placebo. The asterisk (*) indicates p<0.05 versus placebo.

To study the effect of file test compounds as mixtures of enantiomers on body weight, body weight was monitored over time. FIG. 21 shows the change in body weight (in grams) of rat populations that were administered with 75% S-oxprenolol/25% R-oxprenolol at dosages of 40 mg/kg/day; 90% S-oxprenolol/10% R-oxprenolol at dosages of 40 mg/kg/day; or placebo. As shown in FIG. 21, rats receiving 75% S-oxprenolol/25% R-oxprenolol or 90% S-oxprenolol/10% R-oxprenolol had less body weight loss than those receiving the placebo.

Figure 22A:
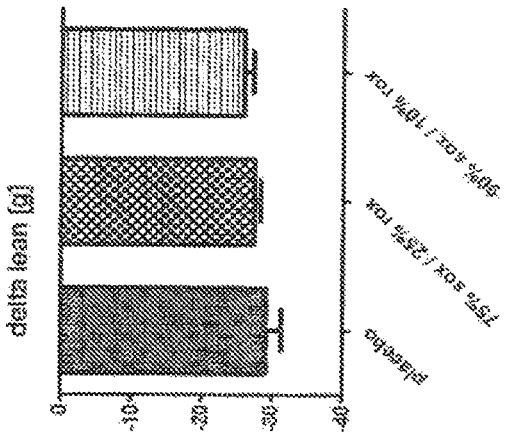
FIG. 22A is a graph showing the change in lean body mass (in grams ("g")) of rat populations that were administered with 75% S-oxprenolol (sox)/25% R-oxprenolol (rox); 90% S-oxprenolol (sox)/10% R-oxprenolol (rox); or placebo.

To study the effect of the test compounds as mixtures of enantiomers on lean body mass, lean mass was determined at the end of the study. FIG. 22A shows the change in lean body mass (in grams) of rats that were administered with 75% S-oxprenolol/25% R-oxprenolol at dosages of 40 mg/kg/day; 90% S-oxprenolol/10% R-oxprenolol at dosages of 40 mg/kg/day; or placebo. As shown in FIG. 22A, rats receiving 75% S-oxprenolol/25% R-oxprenolol or 90% S-oxprenolol/10% R-oxprenolol had less change in lean body mass than those receiving placebo.

Figure 22B:
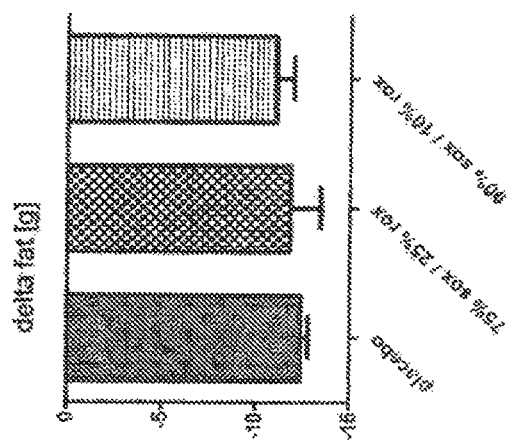
FIG. 22B is a graph showing the change in fat mass (in grams ("g")) of rat populations that were administered with 75% S-oxprenolol (sox)/25% R-oxprenolol (rox); 90% S-oxprenolol (sox)/10% R-oxprenolol (rox); or placebo.

To study the effect of the test compounds as mixtures of enantiomers on fat mass, the fat mass were determined at the end of the study. FIG. 22B shows the change in fat mass (in grams) of rats administered with 75% S-oxprenolol/25% R-oxprenolol at dosages of 40 mg/kg/day; 90% S-oxprenolol/10% R-oxprenolol at dosages of 40 mg/kg/day; or placebo. As shown in FIG. 22B, rats receiving 75% S-oxprenolol/25% R-oxprenolol or 90% S-oxprenolol/10% R-oxprenolol had less fat mass loss than those receiving placebo.

Figure 23:
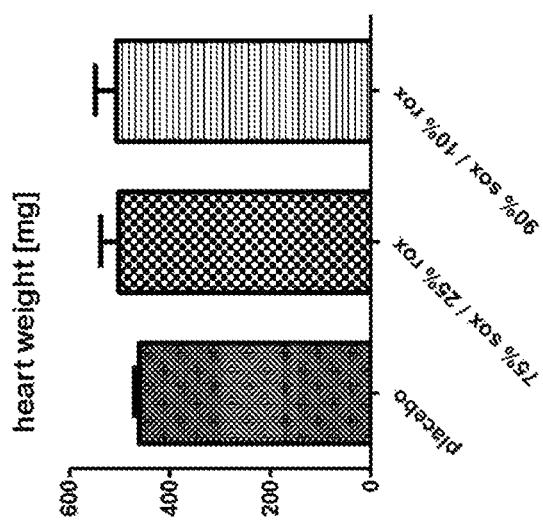
FIG. 23 is a graph showing the mass of heart muscle (in grams ("g")) in rat populations that were administered with 75% S-oxprenolol (sox)/25% R-oxprenolol (rox); 90% S-oxprenolol (sox)/10% R-oxprenolol (rox); or placebo at the endpoint of the study.

To study the effect of the test compounds as mixtures of enantiomers on heart weight, the heart weight was determined at the end of the study. FIG. 23 shows the mass of the heart (in milligrams) of rat populations that were administered with 75% S-oxprenolol/25% R-oxprenolol at dosages of 40 mg/kg/day; 90% S-oxprenolol/10% R-oxprenolol at dosages of 40 mg/kg/day; or placebo. As shown in FIG. 23, rats receiving 75% S-oxprenolol/25% R-oxprenolol or 90% S-oxprenolol/10% R-oxprenolol had more heart mass than those receiving placebo. A higher muscle mass is associated with better muscle function.

Figure 24:
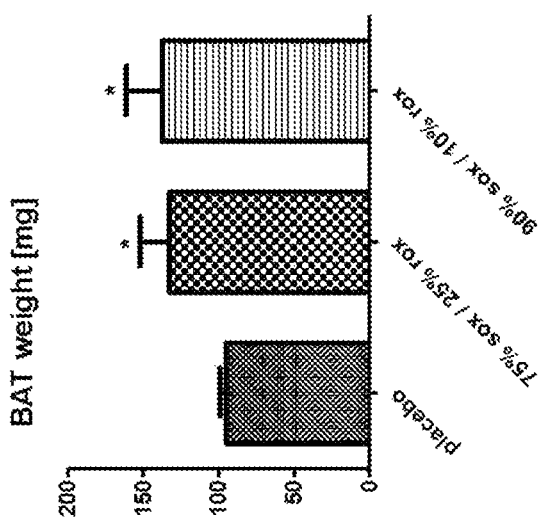
FIG. 24 is a graph showing the weight of brown adipose tissue (BAT) (in grams ("g")) of rat populations that were administered with 75% S-oxprenolol (sox)/25% R-oxprenolol (rox); 90% S-oxprenolol (sox)/10% R-oxprenolol (rox); or placebo at the endpoint of the study. The asterisk (*) indicates p<0.05 versus placebo.

To study the effect of the test compounds as mixtures of enantiomers on fat mass, the fat mass were determined at the end of the study. FIG. 24 shows the weight of brown adipose tissue (BAT) (in grams) of rats administered with 75% S-oxprenolol/25% R-oxprenolol at dosages of 40 mg/kg/day; 90% S-oxprenolol/10% R-oxprenolol at dosages of 40 mg/kg/day; or placebo. As shown in FIG. 24, rats receiving 75% S-oxprenolol/25% R-oxprenolol or 90% S-oxprenolol/10% R-oxprenolol more brown adipose tissue and retained better control of thermogenesis than those receiving placebo.

Figure 25:
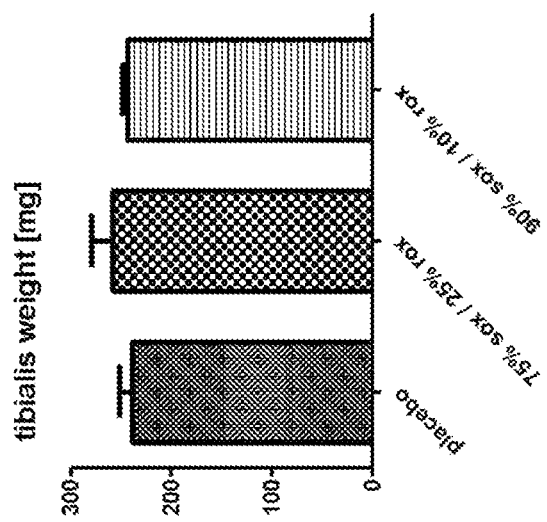
FIG. 25 is a graph showing the mass of tibialis anterior muscle (in milligrams ("mg")) in rat populations that were administered with 75% S-oxprenolol (sox)/25% R-oxprenolol (rox); 90% S-oxprenolol (sox)/10% R-oxprenolol (rox); or placebo at the endpoint of the study.

To study the effect of the test compounds as mixtures of enantiomers on skeletal muscle atrophy, the skeletal muscle mass was determined at the end of the study. FIG. 25 show the mass of tibialis anterior muscle (in milligrams) of rat populations that were administered with 75% S-oxprenolol/25% R-oxprenolol at dosages of 40 mg/kg/day; 90% S-oxprenolol/10% R-oxprenolol at dosages of 40 mg/kg/day; or placebo. A higher muscle mass is associated with better muscle function.

The invention claimed is:

1. A method of treating body weight loss, lean body mass loss and adipose tissue loss in an individual having cancer, wherein the cancer is late stage cancer, comprising administering to the individual an effective amount of a composition comprising oxprenolol or a pharmaceutically acceptable salt thereof, wherein the composition is enantiomerically enriched for S-oxprenolol and comprises an enantiomeric excess of at least about 50% of S-oxprenolol, and wherein the cancer is selected from the group consisting of liver cancer, lung cancer, ovarian cancer, pancreatic cancer, melanoma, brain cancer, gastric cancer, esophageal cancer, colorectal cancer, head and neck cancer, and hematological malignancy.

2. A method of treating muscle wasting in an individual having cancer, wherein the cancer is late stage cancer and in need of treatment of muscle wasting, comprising administering to the individual an effective amount of a composition comprising oxprenolol or a pharmaceutically acceptable salt thereof, wherein the composition is enantiomerically enriched for S-oxprenolol and comprises an enantiomeric excess of at least about 50% of S-oxprenolol, and wherein the cancer is selected from the group consisting of liver cancer, lung cancer, ovarian cancer, pancreatic cancer, melanoma, brain cancer, gastric cancer, esophageal cancer, colorectal cancer, head and neck cancer, and hematological malignancy.

3. The method of claim 1, wherein the composition comprises an enantiomeric excess of at least about 80% of S-oxprenolol.

4. The method of claim 3, wherein the composition comprises an enantiomeric excess of at least about 99% of S-oxprenolol.

5. The method of claim 4, wherein the composition comprises an enantiomeric excess of at least about 99.9% of S-oxprenolol.

6. The method of claim 1, wherein the cancer is liver cancer.

7. The method of claim 1, wherein the composition is administered orally.

8. The method of claim 1, wherein the amount of S-oxprenolol in the composition is about 80 to about 160 mg daily.

9. The method of claim 1, wherein the composition is administered daily or twice daily.

10. The method of claim 2, wherein the composition comprises an enantiomeric excess of at least about 80% of S-oxprenolol.

11. The method of claim 10, wherein the composition comprises an enantiomeric excess of at least about 99% of S-oxprenolol.

12. The method of claim 11, wherein the composition comprises an enantiomeric excess of at least about 99.9% of S-oxprenolol.

13. The method of claim 2, wherein the cancer is liver cancer.

14. The method of claim 2, wherein the composition is administered orally.

15. The method of claim 2, wherein the amount of S-oxprenolol in the composition is about 80 to about 160 mg daily.

16. The method of claim 2, wherein the composition is administered daily or twice daily.

* * * * *